US008119785B2

(12) United States Patent
Avner et al.

(10) Patent No.: US 8,119,785 B2
(45) Date of Patent: Feb. 21, 2012

(54) NUCLEIC ACID SEQUENCES AND HOMOLOGOUS RECOMBINATION VECTORS FOR DISTRUPTION OF A FEL D I GENE

(76) Inventors: David B. Avner, Highlands Ranch, CO (US); Sven Bocklandt, Los Angeles, CA (US); James Kehler, Silver Spring, MD (US)

( * ) Notice: Subject to any disclaimer, the term of this patent is extended or adjusted under 35 U.S.C. 154(b) by 310 days.

(21) Appl. No.: 11/979,151

(22) Filed: Oct. 31, 2007

(65) Prior Publication Data
US 2009/0298168 A1    Dec. 3, 2009

(51) Int. Cl.
*C07H 21/04* (2006.01)
(52) U.S. Cl. .................. 536/23.5; 435/320.1
(58) Field of Classification Search .................. None
See application file for complete search history.

(56) References Cited

U.S. PATENT DOCUMENTS

| | | | |
|---|---|---|---|
| 5,413,923 | A | 5/1995 | Kucherlapati et al. |
| 2003/0177512 | A1 | 9/2003 | Avner et al. |

OTHER PUBLICATIONS http://news.nationalgeographic.com/news/2006/06/060609-allergies-cats_2.html, "Hypoallergenic Cats for Sale, U.S. Firm Announces," Jun. 9, 2006.*
Abbondanzo, "Derivation of Embryonic Stem Cell Lines", Methods in Enzymology, 1993.
Arbones et al., Gene Targeting in Normal Somatic Cells: Inactivation of the Interferon-Gamma Receptor in Myoblasts, Nature Genetics, vol. 6, 90-97, Jan. 1994.
Bradley et al. "Modifying the Mouse: Design and Desire" Bio/technol. 10, 534-539, 1992.
Capecchi, "Altering the Genome by Homologous Recombination", Science, vol. 24, 1989, pp. 1288-1292.
Cibelli et al., Cloned Transgenic Calves Produced for Nonquiescent Fetal Fibroblasts, Science, May 22, 1998, vol. 280, 1256-1258.
Clark et al., "Gene Targeting in Livestock: A Preview," Transgenic Research, vol. 9, pp. 263-275, 2000.
Denning et al., "Gene Targeting in Primary Fetal Fibroblasts From Sheep and Pig," Cloning and Stem Cells, vol. 3, O. 4, pp. 221-231, 2001.
Fulka et al. Cloning by somatic cell nuclear transfer, BioEssays 20:847-851 1998.
Gardner et al., "Reflections on the Biology of Embryonic Stem Cells," Internat. J. Devel., vol. 41, pp. 235-243, 1997.
Gomez et al., "Nuclear Transfer of Synchronized African Wild Cat Somatic Cells Into Enucleated Domestic Cat Oocytes," Biology of Reproduction, vol. 69, pp. 1032-1041, 2003.
Griffith et al, "Current Concepts of PLP and its Role in the Nervous System," Microscopy Research and Technique, vol. 41, pp. 344-358, 1998.
Griffith et al, Expression and genomic structure of the genes encoding Fdl, the major allergen from the domestic cat, Gene 113, 1992, pp. 263-268.

Kato et al., Science 282:2095-98 (1998).
Leonard et al., "Role of the Common Cytokine Receptor Gamma-Chain in Cytokine Signaling and Lymphoid Development, Immunological," Reviews, vol. 148, pp. 98-114, 1995.
Luczynska et al, "Airborne Concentrations and Particle Size Distribution of Allergen Derived from Domestic Cats (*Felis domesticus*)", Measurements Using Cascade Impactor, Liquid Impinger, and a Two-Site Monoclonal Antibody Assay for Fel d I1-4, pp. 361-367.
Lufkin, "Gene Targeting in Mammalian Development and Physiology," Gene Targeting, M.A. Vega, ed 1995 123-147.
Miyoshi et al., Recent Advances in Cloning Technology in the Pig, Asuan-Austral. J. Animal Sci., Feb. 2000, vol. 13, 258-264.
Moreadith, "Gene Targeting in Embryonic Stem Cells: The New Physiology and Metabolism," J. Molecular Med., vol. 75, pp. 208-216, 1997.
Morgenstern et al, "Amino acid sequence of Fel dI, the major allergen of the domestic cat: Protein sequence analysis and cDNA cloning", Proc. Natl. Acad. Sci. USA, vol. 88, pp. 9690-9694 (1991).
Mullins et al., "Perspectives Series: Molecular Medicine in Genetically Engineered Animals," J. Clin. Invest. (1996) vol. 98, S37-S40.
Pennisi et al., "Clones:A hard act to follow" Jun. 9, 2000 vol. 288: 1722-1727 Science.
Polejaeva et al. Cloned pigs produced by nuclear transfer from adult somatic cells Nature pp. 86-90. Sep. 7, 2000.
Prather, Pigs is Pigs, Science, Sep. 15, 2000, vol. 289, 1886-1887.
Prelle et al,. Cells Tissues Organs (1999), vol. 165, 220-236.
Ramirez-Solis et al, "Gene Targeting in Embryonic Stem Cells", Methods in Enzymology, 1993.
Robbins, "Gene Targeting, The Precise Manipulation of the Mammalian Genome", pp. 3-9, Circulation Research, 1993.
Schoonjans et al. (1996) Molec. Reprod. Devel. 45, 439-445.
Shin et al. Nature 415:859 (2002).
Stewart, "Production of Chimeras between Embryonic Stem Cells and Embryos", Methods in Enzymology, 1993.
Thomas et al, "Site-Directed Mutagenesis by Gene Targeting in Mouse Embryo-Derived Stem Cells", Cell, vol. 51, pp. 503-512, 1987.
Verstegen et al, "Superovulation and embryo culture in vitro following treatment with ultra-pure follicle-stimulating hormone in cats", J. Reprod. Fert., Suppl. 47, 1993, pp. 209-218.
Wakayama et al., "Full-term development of mice from enucleated oocytes injected with cummulus cell nuclei," Nature 394:369-74 (1998).
Westhusin et al. Cloning to reproduce desired genotypes, Theriogenology 55:35-49 2001.
Wilmut et al. "Viable offspring derived from fetal and adult mammalian cells," Nature 385:810-13 (1997).
"Post Title.—Allerca Lifestyle Pet Rip-Off", http://www.lifestylepets-ripoff.com/1/post/2008/06/post-title-click-and-type-to-edit.html, Mar. 23, 2010, 5 pages.

(Continued)

*Primary Examiner* — Deborah Crouch
(74) *Attorney, Agent, or Firm* — Clark & Elbing LLP

(57) ABSTRACT

A transgenic cat with a phenotype characterized by the substantial absence of the major cat allergen, Fel d I. The phenotype is conferred in the transgenic cat by disrupting the coding sequence of the target gene with a specialized construct. The phenotype of the transgenic cat is transmissible to its offspring.

16 Claims, 7 Drawing Sheets

OTHER PUBLICATIONS

"The Murky Background of the Ashera and Allerca", http://www.messybeast.com/asheras.htm, Mar. 23, 2010; 10 pages.

Briner et al., "Peripheral T-cell tolerance induced in naïve and primed mice by subcutaneous injection of peptides from the major cat allergen Fel d I", *Proc. Natl. Acad. Sci. USA*, Aug. 1993, pp. 7608-7612, vol. 90, Immunology.

Bronson et al., "Altering Mice by Homologous Recombination Using Embryonic Stem Cells", *The Journal of Biological Chemistry*, (1994) pp. 27155-27158, vol. 269, No. 44, The American Society for Biochemistry and Molecular Biology, Inc., USA.

Chapman et al., "Monoclonal antibodies to the major feline allergen Fel d I. II. Single step affinity purification of Fel d I, N-terminal sequence analysis, and development of a sensitive two-site immunoassay to assess Fel d I exposure", *The Journal of Immunology*, (1988), 4 pages, vol. 140, Issue 3, http://www.jimmunol.org/cgi/content/abstract/140/3/812, American Association of Immunologists.

Crabtree, P., "'Designer pet' founder guilty in British scheme", *The San Diego Union-Tribune*, Oct. 28, 2006, 2 pages, http://legacy.signonsandiego.com/uniontrib/20061028/news_1b28brodie.html.

Desist and Refrain Order (for Violations of Section 31110 of the Corporations Code), to: Simon Brodie, Allerca, Inc., State of California, Business, Transportation and Housing Agency, Department of Corporations, Nov. 2, 2006, 3 pages.

Marian et al., "Expression of a Mutation Causing Hypertrophic Cardiomyopathy Disrupts Sarcomere Assembly in Adult Feline Cardiac Myocytes", *Circulation Research*, 19 pages, http://circres.ahajournals.org/cgi/content/full/77/1/98, American Heart Association.

Neerven et al., "Characterization of cat dander-specific T lymphocytes from atopic patients", *The Journal of Immunology*, (1994), 2 pages, vol. 152, Issue 8, http://www.jimmunol.org/cgi/content/abstract/152/8/4203, American Association of Immunologists.

O'Brien, K., "Bred to be Furry and Allergy-Free—Geneticists and allergists doubtful", *The Boston Globe*, http://www.boston.com/news/local/articles/2007/07/31/bred to be furry and allergy fr . . ., Jul. 31, 2007, 4 pages, USA.

Parronchi et al., "Allergen- and bacterial antigen-specific T-cell clones established from atopic donors shw a different profile of cytokine production", *Proc. Natl. Acad. Sci. USA*, May 1991, pp. 4538-4542, vol. 88, Immunology.

Popken, B., "Simon Brodie, Allerca, Where's My $4,000 Hypoallergenic Cat?", http://consumerist.com/2009/04/allerca-wheres-my-4000-hypoallergenic-cat.htlm, 1 page.

Wang et al., "Specific genetic modifications of domestic animals by gene targeting and animal cloning", *Reproductive Biology and Endocrinology*, Nov. 13, 2003, 8 pages, BioMed Central.

Denning et al., "New Frontiers in Gene Targeting and Cloning: Success, Application and Challenges in Domestic Animals and Human Embryonic Stem Cells," *Reproduction*, vol. 126, pp. 1-11 (2003).

Wang et al., "Specific Genetic Modifications of Domestic Animals by Gene Targeting and Animal Cloning," *Reproductive Biology and Endocrinology*, vol. 1, pp. 1-8 (2003).

Written Opinion for International Search Report for related PCT/US2008/081905 completed Jun. 26, 2009.

Decision on Appeal from U.S. Appl. No. 10/295,903, dated Apr. 25, 2011.

\* cited by examiner

```
GENOMIC SEQUENCE OF Fel d I
Chain 1
ttactagaggatcctgcccacacatacatctccctccctccagcccccaggcagttctgagaagcagcc                         70
                                EXON 1 (LEADER B)
cagagaggcctgcggtgcctcctggaaaagg ATG TTA GAC GCA GCC CTT CCA CCC TGC CCT ACT GTT GCG            140
                                 M   L   D   A   A   L   P   P   C   P   T   V   A
                                -18                         -10
GCC ACA GCA Ggtacaaaagggttccaggctggggagggagcacctgccactgcatc ATG AAG GGG GCT TGT                210
 A   T   A                                                   M   K   G   A   C
             EXON 2 (LEADER A)                              -22 -20     (R)
GTT CTC GTG CTT CTC TGG GCT GCC TTG CTC TTG ATC TCG GGT GGA Agtaggtgtctgggacatgagtgt            280
 V   L   V   L   L   W   A   A   L   L   L   I   S   G   G
                -10                                      (W)
ctgggacacagattctccaggggttcaaacaccttcccaggacacttctgagcatggcgggaaggggaag                        350
ggaagaatgtgtcctgatgaggtctttcaaaagggagggtcagcttgtcttgtgttccagAT TGT GAA                         420
                                                              D/N  C   E
           EXON 3                                              +1
ATT TGC CCA GCC GTG AAG AGG GAT GTT GAC CTA TTC CTG ACG GGA ACC CCC GAC GAA TAT GTT GAG CAA   490
 I   C   P   A   V   K   R   D   V   D   L   F   L   T   G   T   P   D   E   Y   V   E   Q
                                 10                                      20
GTG GCA CAA TAC AAT GCA CTA CCT GTA GTA TTG GAA AAT GCC AGA ATA CTG AAG AAC TGC GTT GAT GCA   560
 V   A   Q   Y   N   A   L   P   V   V   L   E   N   A   R   I   L   K   N   C   V   D   A
        (K)                                                       40
AAA ATG ACA GAA GAG GAT AAG GAG AAT GCT CTC AGC GTG CTG gtgggtctagctctgtgtctgtgcctctga         630
 K   M   T   E   E   D   K   E   N   A   L   S   V   L
        50                                          (L)
cgcctgtctggggggtctgctcaggcagtgcaggaggggggttgctcatgtttgttctccaccatggcc                         700
cttccctgggaatctgggaggagaaagacgccatggctggggaagtagaggggcactcatgtgggcaag                         770
actcagcctacccctcaagctttggggctggcccaggctgctcaacgctgcttggccaccagcttggggg                        840
gctgcaggccctcctatatccctggcatcacttggcctcagtgtcaggccctcagctctggccttcctga                        910
ctccagcctctccagcacgtgagactggatcttcaaactgtttgcactagatgcttcctatctccaaacg                        980
tcagttccttttctcttaactcctcaagttccatattccacccccccccaaaaaaaacctcatctgag                        1050
tcgtcattccctgggtcccagaggccattctgtgcctcaaatactgagagaggaggaggggaggggaggg                       1120
gagaggagaggagaggagaggagaggagaggagaggagaggagaggagaggagaggagaggagaggagag                        1190
gcagcttccaaaaagttctcctgccctgcccaggcctgggatgcctgagtggagaattccagtgaatcct                        1260
ctctctgctgtcccaaagtaggaacaagctactgcttcagcaacaagtgttcaaaggacagaagaaggaa                        1330
gcaggctggaccagctcattcctggagtctccagatgcccacaggtgcatctggagccctgccaggacct                        1400
tcttgccagcgtctctttctaaccaagtctaccacttctatccgagactgccctccatcccatcatagtcac                      1470
ccctcttcttcactctgtttcattggaggaagcttctaggcacaccctgggattctcttgttgtgcagta                        1540
gattgggaagaaccaccttggcctgctcagatccagaagccacccctccaaacaagcctgcaggctcctcc                       1610
ccacaaagtgtccagtgcgtgctcagtagtgttttgtccgttctcacgtaccccctcaaggtctcaccaggt                      1680
                 EXON 4
ctcctgactttctctttgcag GAC AAA ATA TAC ACA AGT CCT CTG TGT TAA aggtaact                        1739
                       D   K   I   Y   T   S   P   L   C   -
                                                  70
```

FIG. 2

```
Chain 2
cacatcctctccaagagctttgtcctcaagagtagaagggcttcccactcttaacagccaagggttgagg        70
agccacccacatgtgccaggtccctgcccacaggcctttggagcttctggcggggggggggtgtgtgggc         140
tgggcttagggtgctagtagtttataaagcagcagaaatcctgtcctgagcagagcattctagcagctga        210
                EXON 1 (LEADER)
cacg ATG AGG GGG GCA CTG CTT GTG CTG GCA TTG CTG GTG ACC CAA GCG CTG GGC GTC AAG ATG Ggtgag 280
     M   R   G   A   L   L   V   L   A   L   L   V   T   Q   A   L   G   V   K   M
    -17                 -10                                              +1
agcagatggagggacagaggaccttcctgatccttgccctgctctatctcactccttcacctcccatggt        350
gatctccaaacaggttctagccacaaagttaagcggccatggggagatcattgtccaggagtcctgcaga        420
accccccctgatgttttagtcgttgaatggagggagaggtttggagatggagggggtcattagtcgtgcac       490
acaataggggagagttagttgggggtagtggtgcttatttgaaaggcagaaacaggcaggctgggatgcc        560
cggagcaccggtcaggggtctctccggctgctctcttctgctgagagtgcctcatagaaaatgttccgtc        630
tgtctgggatgtaagcagtcctgggagtgggcaggtctccgcggaaggtgagtcagaagaccctggatat        700
atgtgagttgctctcaagtggcgggcaaacaggaacctcctgctctgctgattcttttgtgaaggtgttt        770
                                          EXON 2
tctgtttgtgtcttcag CG GAA ACT TGC CCC ATT TTT TAT GAC GTC TTT TTT GCG GTG GCC AAT GGA AAT     840
                     A   E   T   C   P   I   F   Y   D   V   F   F   A   V   A   N   G   N
                                         10                                      20
GAA TTA CTG TTG GAC TTG TCC CTC ACA AAA GTC AAT GCT ACT GAA CCA GAG AGA ACA GCC ATG AAA AAA 910
 E   L   L   L   D   L   S   L   T   K   V   N   A   T   E   P   E   R   T   A   M   K   K
                     30                                      40
ATC CAG GAT TGC TAC GTG GAG AAC GGA CTC ATA TCC AGG GTC TTG GAT GGA CTA GTC ATG gtaatttccta 980
 I   Q   D   C   Y   V   E   N   G   L   I   S   R   V   L   D   G   L   V   M
                     50                                      60
tccttcccgcctcccaaccttcacgttgcgcgtgcagcatattgtaatattccacatacagaccatgc               1050
agtcaggggctaatggcaggtaagagctataaacaatcgagcacataaacctttgctccgcgctctacag            1120
cacatagaatacgcaacctcacgccatgtgcacacccagcctgttcttctaccacacgtgtccctgtgt             1190
gcgaattaccttacgcacagttggaaaatagggggactaatatcggtgtggcatagaaagcgtgttgactc           1260
gtaggattttttctttctaggttaggggtgtcagaattgcaggagtaggattttagccttccacaggaa             1330
agagaaagttcttcattcagctcctgcacatgtaggagccttgtcagttctagttgaggaatattgaaac            1400
taagcacctgccctcagactctcttcccaggaaggggactccctggctttgggaagcttctggttttggc            1470
ttctgtttacttccccttgtgcccaccttgatggctgctattcctttggttcagagtctcacttccttc             1540
tgtatcaattcagggtctaaagtcagtttccactctgtttgttctggtgccctgaggccctcgaggcagc            1610
tcctagctacgtgcagctgcaccccagggctggtcagtgtatttctggtgaactatctttttctgttatt            1680
tttcttgttgcacagttaggtcgattttggttagtctgtctcttacctctacttgccgttaagtgctgat            1750
tctgtaaaatgagagctttgtgaagaagtggaatttcttgcatgactacgggcacccagggcacatggga            1820
ttgttcacaacacacacatacacattccatacatccagtacacctgacagatgagtctcaggtgagggag            1890
acatcgcatggacccagactcagctaccttgcccctcacccaggccatccccatcgcgcctccagaat              1960
cttctcctcttcttgcctcctcactggttgttcaggactcctctggcacaggtgcgtgggtgacgggggg            2030
ggggggggggcgtctccatcctggtctgactgatcgcggccctctctccagaaatcggtctgtgggcta             2100
gaggttcttgctagggacggagcggaatcactgggatgaggcatgaggtgatcctgggggaatggatac             2170
gctgccatgcgctcaggtcttctgtccctcctcgtcttactctctcccag ATA GCC ATC AAC GAA TAT TGC    2240
                                                     I   A   I   N   E   Y   C
                   (EXON 3)                                              70
ATG GGT GAA GCA GTT CAG AAC ACC GTA GAA GAT CTC AAG CTG AAC ACT TTG GGG AGA TGA atctttgcc 2310
 M   G   E   A   V   Q   N   T   V   E   D   L   K   L   N   T   L   G   R   -
                     80                                      90
gctgatgcccttctgagcccatcctcctgtcctgttctttacacctaaagctggaatccagacacctg               2380
tcctcacctaattcactctcaatccaggctgactagaatctcag                                       2425
```

FIG. 3

Schematic representation of sequence replacement for chain 1 or chain 2 of Fel d I

FIG. 4

SEQ ID NO. 7 SCHEMATIC:

SEQUENCE LISTING

```
<160> NUMBER OF SEQ ID NOS: 21

<210> SEQ ID NO 1
<211> LENGTH: 1736
<212> TYPE: DNA
<213> ORGANISM: Felis catus
<220> FEATURE:
<221> NAME/KEY: CDS
<222> LOCATION: (101)..(149)
<220> FEATURE:
<221> NAME/KEY: sig_peptide
<222> LOCATION: (101)..(149)
<220> FEATURE:
<221> NAME/KEY: sig_peptide
<222> LOCATION: (410)..(414)
<220> FEATURE:
<221> NAME/KEY: CDS
<222> LOCATION: (410)..(597)
<220> FEATURE:
<221> NAME/KEY: mat_peptide
<222> LOCATION: (415)..(1725)
<220> FEATURE:
<221> NAME/KEY: CDS
<222> LOCATION: (1699)..(1725)

<400> SEQUENCE: 1
ttactagagg atcctgccca cacatacatc tccctccctc cagcccccag gcagttctga      60
gaagcagccc agagaggcct gcggtgcctc ctggaaaagg atg tta gac gca gcc     115
                                            Met Leu Asp Ala Ala
                                                            -15 ctt cca ccc tgc cct act gtt gcg gcc aca gca g gtacaaagg              159
Leu Pro Pro Cys Pro Thr Val Ala Ala Thr Ala
       -10                   -5 gttccaggct ggggagggag cacctgccac tgcatcatga aggggcttg tgttctcgtg     219
```

```
cttctctggg ctgccttgct cttgatctcg ggtggaagta ggtgtctggg acatgagtgt      279
ctgggacaca gattctccag gggttcaaac accttcccag ggcacttctg agcatggcgg      339 gaagggaag ggaagaatgt gtcctgatga ggtctttcaa aagggagggt cagcttgtct       399
tgtgttccag at  tgt gaa att tgc cca gcc gtg aag agg gat gtt gac         447
            Asp Cys Glu Ile Cys Pro Ala Val Lys Arg Asp Val Asp
             -1  1               5                  10 cta ttc ctg acg gga acc ccc gac gaa tat gtt gag caa gtg gca caa         495
Leu Phe Leu Thr Gly Thr Pro Asp Glu Tyr Val Glu Gln Val Ala Gln
            15              20                  25 tac aat gca cta cct gta gta ttg gaa aat gcc aga ata ctg aag aac         543
Tyr Asn Ala Leu Pro Val Val Leu Glu Asn Ala Arg Ile Leu Lys Asn
            30              35                  40 tgc gtt gat gca aaa atg aca gaa gag gat aag gag aat gct ctc agc         591
Cys Val Asp Ala Lys Met Thr Glu Glu Asp Lys Glu Asn Ala Leu Ser
        45              50                  55 gtg ctg gtgggtctag ctctgtgtct gtgcctctga cgcctgtctg gggggtctgc          647
Val Leu
60 tcagggcagt gcaggagggg ggttgctcat gtttgttctc accatggcc cttccctggg        707 aatctgggag gagaaagacg ccatggctgg ggaagtagag gggcactcat gtggggcaag       767 actcagccta cccctcaagc tttggggctg gcccaggctg ctcaacgctg cttggccacc       827 agcttggggg gctgcaggcc ctcctatatc cctggcatca cttggcctca gtgtcaggcc       887 ctcagctctg gccttcctga ctccagcctc tccagcacgt gagactggat cttcaaactg       947 tttgcactag atgcttccta tctccaaacg tcagttcctt ttctcttaac tcctcaagtt      1007 ccatattcca cccccccccc caaaaaaaac ctcatctgag tcgtcattcc ctgggtccca      1067 gaggccattc tgtgcctcaa atactgagag aggaggaggg gaggggaggg gagaggagag      1127 gagaggagag gagaggagag gagaggagag gagaggagag gagaggagag gagaggagag      1187 gcagcttcca aaaagttctc ctgccctgcc caggcctggg atgcctgagt ggagaattcc      1247 agtgaatcct ctctctgctg tcccaaagta ggaacaagct actgcttcag caacaagtgt      1307 tcaaaggaca gaagaaggaa gcaggctgga ccagctcatt cctggagtct ccagatgccc      1367 acaggtgcat ctggagccct gccaggacct tcttgccagc gtctttctaa ccaagtctac      1427 cacttctatc cgagactgcc ctccatccca tcatagtcac ccctcttctt cactctgttt      1487 cattggagga agcttctagg cacacccctgg gattctcttg ttgtgcagta gattgggaag     1547 aaccaccttg gcctgctcag atccagaagc caccctccaa acaagcctgc aggctcctcc      1607 ccacaaagtg tccagtgcgt gctcagtagt gtttgtccgt tctcacgtac ccctcaaggt      1667 ctcaccaggt ctcctgactt tctctttgca g gac aaa ata tac aca agt cct         1719
                                   Asp Lys Ile Tyr Thr Ser Pro
                                                       65 ctg tgt taaaggtaac t                                                    1736
Leu Cys
    70

<210> SEQ ID NO 2
<211> LENGTH: 88
<212> TYPE: PRT
<213> ORGANISM: Felis catus

<400> SEQUENCE: 2

Met Leu Asp Ala Ala Leu Pro Pro Cys Pro Thr Val Ala Ala Thr Ala
        -15                 -10                  -5
```

```
Asp Cys Glu Ile Cys Pro Ala Val Lys Arg Asp Val Asp Leu Phe Leu
 -1   1               5                  10

Thr Gly Thr Pro Asp Glu Tyr Val Glu Gln Val Ala Gln Tyr Asn Ala
 15              20                  25                  30

Leu Pro Val Val Leu Glu Asn Ala Arg Ile Leu Lys Asn Cys Val Asp
                 35                  40                  45

Ala Lys Met Thr Glu Glu Asp Lys Glu Asn Ala Leu Ser Val Leu Asp
             50                  55                  60

Lys Ile Tyr Thr Ser Pro Leu Cys
             65                  70

<210> SEQ ID NO 3
<211> LENGTH: 2425
<212> TYPE: DNA
<213> ORGANISM: Felis catus
<220> FEATURE:
<221> NAME/KEY: CDS
<222> LOCATION: (215)..(275)
<220> FEATURE:
<221> NAME/KEY: sig_peptide
<222> LOCATION: (215)..(265)
<220> FEATURE:
<221> NAME/KEY: mat_peptide
<222> LOCATION: (266)..(2298)
<220> FEATURE:
<221> NAME/KEY: CDS
<222> LOCATION: (788)..(969)
<220> FEATURE:
<221> NAME/KEY: CDS
<222> LOCATION: (2221)..(2298)

<400> SEQUENCE: 3
cacatcctct ccaagagctt tgtcctcaag agtagaaggg cttcccactc ttaacagcca      60
agggttgagg agccacccac atgtgccagg tccctgccca caggcctttg agcttctgg     120 cggggggggg gtgtgtgggc tgggcttagg gtgctagtag tttataaagc agcagaaatc    180
ctgtcctgag cagagcattc tagcagctga cacg atg agg ggg gca ctg ctt gtg    235
                                      Met Arg Gly Ala Leu Leu Val
                                                              -15 ctg gca ttg ctg gtg acc caa gcg ctg ggc gtc aag atg g gtgagagcag    285
Leu Ala Leu Leu Val Thr Gln Ala Leu Gly Val Lys Met
-10                  -5                  -1   1 atggagggac agaggacctt cctgatcctt gccctgctct atctcactcc ttcacctccc    345
atggtgatct ccaaacaggt tctagccaca aagttaagcg ccatggggga gatcattgtc    405
caggagtcct gcagaacccc cctgatgttt ttagtcgttg aatggaggga gaggtttgga    465
gatggagggg tcattagtcg tgcacacaat aggggagagt tagttggggg tagtggtgct    525
tatttgaaag gcagaaacag gcaggctggg atgcccggag caccggtcag gggtctctcc    585
ggctgctctc ttctgctgag agtgcctcat agaaaatgtt ccgtctgtct gggatgtaag    645
cagtcctggg agtgggcagg tctccgcgga aggtgagtca gaagaccctg atatatgtg    705 agttgctctc aagtggcggg caaacaggaa cctcctgctc tgctgattct tttgtgaagg    765
tgttttctgt tgtgtcttc ag cg  gaa act tgc ccc att ttt tat gac gtc      816
                             Ala Glu Thr Cys Pro Ile Phe Tyr Asp Val
                                  5                  10 ttt ttt gcg gtg gcc aat gga aat gaa tta ctg ttg gac ttg tcc ctc      864
Phe Phe Ala Val Ala Asn Gly Asn Glu Leu Leu Leu Asp Leu Ser Leu
            15                  20                  25 aca aaa gtc aat gct act gaa cca gag aga aca gcc atg aaa aaa atc      912
Thr Lys Val Asn Ala Thr Glu Pro Glu Arg Thr Ala Met Lys Lys Ile
 30                  35                  40                  45
```

```
cag gat tgc tac gtg gag aac gga ctc ata tcc agg gtc ttg gat gga      960
Gln Asp Cys Tyr Val Glu Asn Gly Leu Ile Ser Arg Val Leu Asp Gly
            50                  55                  60 cta gtc atg gtaatttcct atccttcccc gcctccccaa ccttcacgtt             1009
Leu Val Met gcgcgtgcag catattgtaa tattccacat acagaccatg cagtcagggg ctaatggcag   1069
gtaagagcta taaacaatcg agcacataaa cctttgctcc gcgctctaca gcacatagaa   1129
tacgcaacct cacgccatgt gcacacccag cctgttcttc taccacacgt gtcccttgtg   1189
tgcgaattac cttacgcaca gttggaaaat aggggactaa tatcggtgtg gcatagaaag   1249
cgtgttgact cgtaggattt ttttctttct aggttagggg tgtcagaatt gcaggagtag   1309
gattttagcc ttccacagga aagagaaagt tcttcattca gctcctgcac atgtaggagc   1369
cttgtcagtt ctagttgagg aatattgaaa ctaagcacct gccctcagac tctcttccca   1429
ggaagggact ccctggcttt gggaagcttc tggttttttgg cttctgttttt acttcccctt  1489 gtgcccacct tgatggctgc tattcctttg gttcagagtc tcacttcctt ctgtatcaat   1549
tcagggtcta aagtcagttt ccactctgtt tgttctggtg cctgaggccc tcgaggcagc   1609
tcctagctac gtgcagctgc accccagggc tggtcagtgt atttctggtg aactatcttt   1669
ttctgttatt tttcttgttg cacagttagg tcgattttgg ttagtctgtc tcttacctct   1729
acttgccgtt aagtgctgat tctgtaaaat gagagctttg tgaagaagtg gaatttcttg   1789
catgactacg ggcacccagg gcacatggga ttgttcacaa cacacacata cacattccat   1849
acatccagta cacctgacag atgagtctca ggtgagggag acatcgcatg gacccagact   1909
cagctacctt gcccctcacc caggccatcc ccatcgcgcc ctccagaatc ttctcctctt   1969
cttgcctcct cactggttgt tcaggactcc tctggcacag gtgcgtgggt gacgggggg    2029 gggggggggg gcgtctccat cctggtctga ctgatcgcgg ccctctctcc agaaatcggt   2089
ctgtgggcta gaggttcttg ctagggacgg agcggaatca ctggggatga ggcatgaggt   2149
gatcctgggg gaatggatac gctgccatgc gctcaggtct tctgtccctc ctcgtcttac   2209
tctctcccca g ata gcc atc aac gaa tat tgc atg ggt gaa gca gtt cag     2259
             Ile Ala Ile Asn Glu Tyr Cys Met Gly Glu Ala Val Gln
                 65                  70                  75 aac acc gta gaa gat ctc aag ctg aac act ttg ggg aga tgaatctttg       2308
Asn Thr Val Glu Asp Leu Lys Leu Asn Thr Leu Gly Arg
     80                  85                  90 ccgctgatgc cccttctgag ccccatcctc ctgtcctgtt ctttacacct aaagctggaa   2368
tccagacacc tgtcctcacc taattcactc tcaatccagg ctgactagaa tctgcag      2425

<210> SEQ ID NO 4
<211> LENGTH: 107
<212> TYPE: PRT
<213> ORGANISM: Felis catus

<400> SEQUENCE: 4

Met Arg Gly Ala Leu Leu Val Leu Ala Leu Leu Val Thr Gln Ala Leu
        -15                 -10                  -5

Gly Val Lys Met Ala Glu Thr Cys Pro Ile Phe Tyr Asp Val Phe Phe
 -1  1               5                  10                  15

Ala Val Ala Asn Gly Asn Glu Leu Leu Leu Asp Leu Ser Leu Thr Lys
                20                  25                  30

Val Asn Ala Thr Glu Pro Glu Arg Thr Ala Met Lys Lys Ile Gln Asp
            35                  40                  45

Cys Tyr Val Glu Asn Gly Leu Ile Ser Arg Val Leu Asp Gly Leu Val
```

```
            50                  55                   60
Met Ile Ala Ile Asn Glu Tyr Cys Met Gly Glu Ala Val Gln Asn Thr
            65                  70                   75

Val Glu Asp Leu Lys Leu Asn Thr Leu Gly Arg
80                   85                   90

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gccaatatgg gatcggcc                                                    18

<210> SEQ ID NO 6
<211> LENGTH: 8
<212> TYPE: PRT
<213> ORGANISM: Felis catus

<400> SEQUENCE: 6

Thr Thr Ile Ser Ser Ser Lys Asp
1               5

<210> SEQ ID NO 7
<211> LENGTH: 21939
<212> TYPE: DNA
<213> ORGANISM: Felis catus

<400> SEQUENCE: 7
attcaaatac aaactttacc ctcaacaaca tttcattata ttcaaatata cataaattat      60
aataattcta ataaaaaaaa cacggaaata atacaattaa ttgatataaa ttatcacaaa     120
tataaagatt aaaaattcca tttactaaat actcaatcta aattattaat cttactatta     180
aaacctattt catatataat tttaactcat cttcaacttt aattaaatat gtcactttat     240
taaatcttat tacttaacac taacattata tattccacta tgtaacctag taataataca     300
tataatgtca caactgaaaa acatatcata taaaaaaaaa aaaatttca aaacaaaacg      360 cgataaagaa caacaccagc atcggaccag aaaacagcca aaactatacc ctcaaccatg     420
tacagaaatt taccaacaaa tcaaagtcca acgccgtatt tgtagtctct agaagtgaga     480
tcaagtccga agctatagtc ggacactcac cccatcgttc cgcacagacg ccccaaccaa     540
gaactatttt aaacgataca accagacatc cggaaaggtt cacagcaaca ttatttgtcg     600
tagccaaaaa aggtgggaag gacccagatg cccatcacag atgaacggat aaataagaag     660
tggtctctcc aagcaatggg atatgatttg actctaagaa ggaatcaagt agtaatgtat     720
actaccacat ggaagaatct tgaacaagtg ctgagcacaa gaagccagtc acaaaaggcc     780
tgattctatc cacaggaaac gtccagaaca ggcaaatcca gactggtggt tgccagggcc     840
tgggagaggt gaatgggag tgatagctaa caggcacagc gtttattttg ggggtgaata      900
aaatgtctgg aattcaagaa ctgtgatggt tgtacaacct gatgaatata ccagaaaaca     960
ctgaactgtc ctcaagagta aatgaactta caggacatga gttgtatcac gataaagctg    1020
ttacacctgt ttgcagacag ctgtggagaa acaggcccat ccctccactt ccagagcttt    1080
ctgcgttggc cagacctcca aagagtcact tggccgagga gagcgctct gggaatgtag      1140 cccaaagaaa accacacaca gctgggcatg gcaggctgca gccacagtgt ttctgatact    1200
```

```
aaacaaagtc cagctagctc aggggccctg ggcatgggcg aggttgcgtc tggtgtgcat    1260
ttctctggaa ttaagtggca acccttctgt tcagctttca aaggcatccg aagctgaca     1320 aaggtcgaga gacgcatcag gctctctgct gtcagcttga agcctgcttc tgatcctcgg    1380 tcccctctc  tctctgcccc tcacctgctt gccctgtctc tctctctctc aaaaataaaa    1440
acataataat aataattttt aaaaacttaa aaaaaaaaa agagtaagag gcaagccacg     1500
gaccgggagg aaacgtttac aaaacacgta tctgatgaag gacttgtatc caaaataaat    1560
gaagagctct taaaattcta tgataacgac caacatgaaa acgggcaaaa ggtatggaca    1620
cctcatgaaa caagacacac agacggtaaa taagcatatg ggaagatgtg caccatcaca    1680
ggccaccagg ggactgcaaa ttagaaccac ggcagtgaca ccactgtcag gagtggaaca    1740
gcaggacctc tctcactgct ggtggggacg caacacggtg tggccgcttt ggaagacggt    1800
ttggcagttt cctacaaaac taactacccg gggtgcctgc gggggggctc agtcagttag    1860
gcgtccaact tcagctcagg tcatgatctc tcagtctgtg agttcgagcc ccgcatcggg    1920
ccctgtgctg acagcttgga gcccggagcc tgcttcagat tctgtgtctc cctctctctc    1980
tgcccctccc ttgctcatgc tctgtctctc tgtctttcaa aaacaaataa atgttaaaaa    2040
aaaatttttt taaccgaact gtacccttta attttaacta actatattct actctctact    2100
gcattaatga tgtaaaattt agtaggtaca tggaagcaat taaagaaaaa tcaagtaaaa    2160
aaaactattg ttggtttgaa ttgttggtta ttgaattaag aatcttagtg gggcgcctgg    2220
gtggctcagt tgagcgtccc actcttgatc gcagctcagg tcagatctca cggtttgtga    2280
gttcgagccc cacatcgggc tccacactga caacacacag cctgcttggg attctttctc    2340
tctccttctc tctcccctcc cccactcgca tgcactctct ctctctcaaa acaaacttta    2400
aaaaaaaaga ataaaaattt aaaaaaagga tcaataacca cgatcgagtg ggatttgatc    2460
cagagactca aggatgattc aatatcctac aaatcaatca acgtgacata ccacaagaac    2520
aaaaaaatga aggaagaagt gaaatcgacc aaaacaaatc atacaaatac tgtatgattt    2580
cccttatgcg tagaatctaa aaaaataaaa caaaaaacca acaagataac agactcataa    2640
atagagacaa atatcatcaa gaatagtgta ataactccgt atggtaacag acggtcacgg    2700
cacttagggt gaacatttcg tcacgtatgt aaatgtccat ccactatgtt gtacacctga    2760
aactaataca atagtgtgac aactacgctc aattaaaaaa aagaatattg gcaacatgtt    2820
tcagatacca cgggatcaat taggcagctt caggctggct tgtgagtgtt accacctcag    2880 cttttcataag gcacacgaca tagtgggctc agcctgtcat caacggaggc agagcaccaa    2940
tcaaacagga cttagtttcc tgagacacgg gaggacacca gaaagcagtg tcgccgttaa    3000
agctctggat tccaaacaca agccacatct gagcgaacac agcaccagca cagccaaaaa    3060
cacacacaaa aagtgtggca tttactgaga atgatggcca cccacgctcg ctcaccctga    3120
tcagttacaa ggctacaatt tccatctgct aagtgcccac aaggtaatga aatatttagc    3180
tggctcgaag agagactgga ttggaagcct ggggactttc aataggtgga gagaggggca    3240
gggtacgtct ccagcatgcc ccctacagac cccagctggg gtgtgccaag gcaggccagg    3300
acaggggttg agggatcaga aacgaacccc aagcattttc cagtcccgtg ccctgaatga    3360
cagcaaagca ctcacaccag gtgcccttct aagacccatc agacaaatct tacggggcg     3420 aggacttcag ggtcttctcc cagacccagg gagcaacgcc ctgacctcgc ggcatcagga    3480
cacgcatgtt ccctaaggct cagagacgcc ctcagcatcg tgctgacttt gggagacaca    3540
tcacacctta gactttttaat cctacccatt cataagccaa agtaaacaac aggccatttc    3600
```

-continued

```
tggggcagcg ggcgggctgg agctgtctcc accacctgcc ccctcccttt acagcagcat    3660
ttgcccctgg tcagggcagg cgatgaggta cagagactcg gtgtcaagac ctgggtttca    3720
gtgtccactg gtcactcccg cactcggttt accctatccc taaaacgagg gtgattcctg    3780
tgcacccccc ccccccgggg gctgagagct acgcaagcga gcttgaaggg tgcagggtgt    3840
agatgggagc cggggcgagc tctcagaacg caggttttgc ccctgaacac agggccgctc    3900
ccctgtcagc tgatgtcagg cttgctcca catcaagacg tgagaaaat aagtttatt      3960
acaaaagcag ttctttctcc cgatgcttca acctcccagt ctgatgttat ctccccggct    4020
ggattaaaat tctgatttgc tagggcgcct gggtggctca gttggtgaaa catctgactt    4080
tggctcaggt catgatctcg cagttcatga gttcaggccc catgtccacc tctgtgctga    4140
cagctcagag cctggagcct gcttcggatt ctgtgtctcc ctctctctgt ctcccactca    4200
cactctgtct ccctctcaaa aataaataaa catgaaaaag aaaattctaa tttccctggg    4260
gcacctggga agctcagtta gttaagcatc tgactttggc tcaggtcatg atctcttagt    4320
tcgtgagttc aagcccctca ttgcatcggg ctgtctgctc tcagctgtct gctctcagca    4380
cagagcacgc tttggatcct ctgtctccct ctctctctgc ccctccccag cttgttctct    4440
cactctctct ctctctctct ctctctctct ctcaaataaa taaataaaca ttaaaaaga    4500
ttaagatata tgagatctct ctagatgaaa atatggggcc gttggatgta ataaaatgaa    4560
aattcaggaa gaaatctcat caaatgacat caatagctac aatattcaaa tagaagatta    4620
accaaaagtc cttaattacg aagctcaaag ttcaggcta tctacaaact cacgaaaacg     4680
tccaaagtcg aaatgcgtgg caggtgaggc ctgaacggac ggctgccccc accgtgctgc    4740
atgcactgcc cccccacaga gaggccgccc cgatgacact cccctgacct cagctagcct    4800
gacattcaga tgacccatcc agggcgggca caggaagccc cttcccactt caaacttgcg    4860
gccccacagc gtcacagtcc cctgcaccac atcctgaggg gagaggagag gccacccagg    4920
cgggtcaggg agcatctggc tttagtggac agtggacagt gtcccttgc cgggttccat     4980
tccgccgtga ccacaggcac atttaccgac tcggagccag aggcaccgct tttaaaaaat    5040
gctgcttctt gggacgcctg ggtggctcag tgggttaagt gtctgacttc ggctcaggtc    5100
atgatctcac agtccgtgag ttccagccct gtgtcgcgct ccatgctgac agttcggagc    5160
ctgcttggga ttctctgtct tcctctctct ttgcccctcc tccacttgcg ctgtctctgt    5220
ctttctcaaa ataaataaac ttaaaacatc ttttaatatg taagacttta acttatctgg    5280
agtttatttt gaagaaaact gtaagtgagg tatccaatag tttgatttcc ccaaatgttc    5340
aatcaattga tccagcacca ttccacttat gaaataatcc taatttcttc acttacttgc    5400
aagttacctt tatcataaaa tccaggatta tttacaccta tgtctggcct tcttttcgca    5460
gtccatttat ctgcctgtgt ttatgtttta atatttcata ggggcaccta ggtggctcag    5520
tcagttgagc atccaactct tggtttcagt tcaggtcatg atcccagggt cgagcccga    5580
gtcgggatcc gtgctgggca tggaggctgc ttgggattct ctctctccct ctgaccctct    5640
cccctgctca tgtgcgctct ctctctctca aatataagta aataaataaa ttttagtatt    5700
tcataggcct tgctgcccct gattttgttt taaaattttt gttcaggggc gcctggtggc    5760
tcagttggtt aagtggccaa ctcttgattg cagctcaggt catgatctca agattcgtgg    5820
gattgagtcc catgtcaggc tctgcgctgg acatgaaaac tgcttaagat tctctctccc    5880
tctccctctc cctctgcctc tccctgctc actctctctc tttcaaaaaa atttttttaa    5940
ataaagtact tttttcttca aaaaaatcct gttcaaaaat ccagtttata aaaaaataaa    6000
```

```
taaactgtta tttttggagg gaaatgacat atttatgctg ttcaaaattc ccattcaaat    6060
cttttgttta tttaagtcct ctgtatattt gggcctgagg aggaatttag ggttttttca    6120
atattaatta attcaacaaa tatttagtga gagccaattt tgtgccttta agtgttttag    6180
tactgggttt ggagatttaa atttggaaga aagtaagtct gtatagaaaa gagatgcaaa    6240
gacaatgatc gcttgtgtaa gacacaagta accagaaaaa aagctgagaa agatgcccca    6300
ataagagaga gaaaaaccaa cagactatga tatcacggaa gtcaaaagag agagacagag    6360
atcactcatg acaaatggat aattaactat tggaactttg gcaattaagt cattaatcca    6420
cagggaaagg cttggcagat ccatcttcat ttcttaaata ttttggtcat tttgttcaat    6480
gccacttaaa aaaaatccat tctttctcca tgactcaata agctgtcact attatatctt    6540
aaactttctt tgagtctatt tgtgtgtttt ctcttctatc acaacgacca tccatttctc    6600
tactgaaact agattaattg ttagtcttat acctatgttg tgatacctgg tgagaaagat    6660
cttgctcatg gttcttattt ttctaaattg tcttgcttga tgtcaattca agaatttatt    6720
cttggggcgc ctgggtggcg cagtcggtta agcgtccgac ttcagccagg tcacgatctc    6780
gcggtctgtg agttcgagcc ccgcgtcggg ctctgggctg atggctcaga gcctggagcc    6840
tgtttccgat tctgtgtctc cctctctctc tctgctcctc ccccgttcat gctctgtctc    6900
tctctgcccc aaaataaat aaacgttgaa aaaaaattta aaaaaaaaa gaatttattc    6960
ttttggagga actttaaatc aatcttcatt agaacaaaga ttaatttaga tggctttggg    7020
aatagttgac atgtctatag tgtcaatttg tcccctacga tagccgggat gatgatttag    7080
cccccttacca attcaaattc tattttgtac ttctcaataa aattgtagac ctttagtctg    7140
acctgaacag ttaatgttag gtctagcaga cttggtaggt gtgaaaccca gatgtaaaat    7200
gagtgaacag gtgaattaaa atgcttaagt tcaaccacta ggccagagaa gagccagatc    7260
tcccccatga cagccattcc ctctgggtta gtttcttcca tccacttctt ttctcccttc    7320
ctcctgagcc aagactgcat aggggtcatg gttccgctgg cagaacccaa gaacagcagt    7380
ggaactgaga gttcctgcag aaaggttggc ctcctcagaa gacatctacc aaagaagcag    7440
aaaatggtgg ggtagcctgg gtggctcagt cggttaaagt gtccaacttc ggctcaagtc    7500
atgatctcac agtttgtggg tctgagaccc gtgctctctc tctctctctc tctctctctc    7560
tctctctctc tgccccttcc cacttgtgtg cgctctctct ctctttctct caaaaataaa    7620
cattaagaaa ttttttttaaa aacgaagcag aaaaatggca ataccactg agacacggat    7680
agtagaggat ttgtgataaa cccactcagg tcatcacctg agtcacccttt aaattgccag    7740
ggtgacactt tttttaacgt ttatttttaa gagagagggt gagcgcttgc acacgtgcaa    7800
gtgggggagg ggcagagaga gggagacaca gactccaaag cgggattcag gcatgagctg    7860
tcagcacagg gcctgatgcc ccgctcgaac tcacaaacct tgagatcatg acctgagctg    7920
aagtcggtca cctaaccaac tgagccaccc aggcgcccct gccaggatga catttaaggg    7980
agtagaggct ctgctgctgt gacaaatgcc agagttggaa atatgctacg tggacaacat    8040
ttttatcctt ccgtggtgat gaatcctggg gtcacatgta tgtgatttaa tttaatcctc    8100
acacttaatc cccatttgc agatgagaga atagcccgag gaagaggaaa ccgctcacat    8160
gtgctcctga ttcagcctgc ctccagtccc catgctctca atgagcacat gtcacctccc    8220
tttgccatgt cccaggatct cctgccaggc ctcccacgct tcccgcacag aacacagaca    8280
cggggcaccc gggggtgcta agatgcagtt attttattct agtcagcctg attgagagtg    8340
aattaggtga ggacaggtgt ctggattcca gctttaggtg taaagaacag gacaggagga    8400
```

```
tggggctcag aagggcatc agcggcaaag attcatctcc ccaaagtgtt cagcttgaga      8460
tcttctacgg tgttctgaac tgcttcaccc atgcaatatt cgttgatggc tatctgggag      8520
agagtaagac gaggagggac agaagacctg agcgcatggc agcgtatcca ttcccccagg      8580
atcacctcat gcctcatccc cagtgattcc gctccgtccc tagcaagaac ctctagccca      8640
cagaccgatt tctggagaga gggccgcgat cagtcagacc aggatggaga cgcccccccc      8700
cccccccccc gtcacccacg cacctgtgcc agaggagtct gaacaaccag tgaggaggca      8760
agaagaggag aagattctgg agggcgcgat ggggatgggc ctgggtgagg ggcaaggtag      8820
ctgagtctgg gtccatgcga tgtctccctc acctgagact catctgtcag gtgtactgga      8880
tgtatggaat gtgtatgtgt gtgttgtgaa caatcccatg tgccctgggt gccgtagtc       8940
atgcaagaaa ttccacttct tcacaaagct ctcattttac agaatcagca cttaacggca      9000
agtagaggta agagacagac taaccaaaat cgacctaact gtgcaacaag aaaaataaca      9060
gaaaaagata gttcaccaga aatacactga ccagccctgg ggtgcagctg cacgtagcta      9120
ggagctgcct cgagggcctc aggcaccaga acaacagagt ggaaaatctg actttagacc      9180
ctgaattgat acagaaggaa gtgagactct gaaccaaagg aatagcagcc atcaaggtgg      9240
gcacaagggg aagtaaaaca gaagccaaaa accagaagct tcccaaagcc agggagtccc      9300
ttcctgggaa gagagtctga gggcaggtgc cttagtttca atattcctcc accagaactg      9360
acaaggctcc tacatgtgca ggagctgaat gaagaacttt ctctttcctg tggaaggcta      9420
aaatcctact cctgcaattc tgacaccccg aacctagaaa gaaaaaaatc ctacgagtca      9480
acacgctttc tatgccacac cgatattagt ccctattttt ccaactgtgc gtaaggtaat      9540
tcgcacacaa gggacacgtg tggtagaaga acaggctggg tgtgcacatg gcgtgaggtt      9600
gcgtattcta tgtgctgtag agcggagcaa aggtttatgt gctcgattgt ttatagctct      9660
tacctgccat gtagcccctg actgcatggt ctgtatgtgg aatattacaa tctgctgcac      9720
gcgcaacgtg aaggttgggg aggcggggaa ggaaaggaaa ttaccatgac tagtccatcc      9780
aagaccctgg ataagagtcc gttctccacg tagcaatcct ggatttttt catggctgtt        9840
ctctctggtt cagtagcatt gacttttgtg agggacaagt ccaacagtaa ttcatttcca      9900
ttggccaccg caaaaaagac gtcataaaaa atggggcaag tttccgctga agacacaaac      9960
agaaaacacc ttcacaaaag aatcagcaga gcaggaggtt cctgtttgcc cgccacttga     10020
gagcaactca catatatcca gggtcttctg actcaccttc cgcagagacc tgcccactcc     10080
caggactgct tacatcccag acagacgaaa cattttctat gaggcactct cagcagaaga     10140
gagcagccgg agagaccct gaccggtgcc tccgggcacc ccagcctgcc tgtttcggcc      10200
tttcaaataa gcaccactac ccccaactaa ctctcccctc ttgtgtgcac aactaatgat     10260
ccctccatct ccaaacctct ccctccattc tacgactaaa acatcagggg gggttctgca     10320
ggactcctgg acaatgatct cccagctgcc gcttaacttt gtggctagaa cctgtttgga     10380
gatcaccatg ggaggtaaag gagtgagata gagcaggcaa ggatcaggaa ggtcctctgt     10440
ccctccatct gctctcaccc atcttgacgc ccagctcttg ggtcaccagc aatgccagca     10500
caagcagtgc ccccctcatc gtgtcagctg ctagaatgct ctgctcagga caggatttct     10560
gctgctttat aaactactag caccttaagc ccagcccaca ccccccccc ccagaagctc      10620
caaaggcctg tgggcaggga cctggcacat gtgggtggct ccctcaaccc ttgggctgtt     10680
aagagtggga agcccttcct actcttgagg acaaagctct tggagaggat gtggtttttt     10740
cttttgccaaa gaccaactgg aggtgatgtg tctaagtgat tccatgctga gccaactgct     10800
```

```
ctgttgtccc agctccaact gtcacccctg tttcctgcta ctccttccct caaactatcc   10860
tggttcccaa atgcgatact ctcccaagac aaagagataa aaatcacagg aggggtcaag   10920
gacaggtcta caccactaca ggtagacaaa aaatcatcca aaaaccttac ttgtgcccaa   10980
gtttaagtcc tggagataag tatggggtgc tagacccacc tcaagcctct tgaacacctt   11040
aactgctgca gtctgtggat caagccctga gaatgggtgg acaccatcct tgggctacaa   11100
atcactccct actaggggag tctcaggacg cttgggcatg taggcctcct caagggctgg   11160
taacgctcta aattaggatc atgtcacctg cttccctctc acccttaagg aagtaaatgc   11220
ctgggcacct tcttgactcc aagtagctcc aggtttggcc ctgtctcacc ctcctccatc   11280
agtaaactta atcccaagag gaggttggac ttactagccc atccagaaac attagtgaat   11340
agttgtgggg ttgtacagtt tgtctcttat gtccattgtg agttggagct ccacatacca   11400
aggtgccagg tcaaccaaag gtgcttaagc gctctcaaga gctaaactga accttctaat   11460
ctaggaaagt agtttatcgg cacaaacatg acgagatagt ccatgaaaat tattgaagga   11520
aactcccagt ggccaaatct gaaacaattt gagcaaacaa agaaataac attgtattgg    11580 ttgataaccc aaagtataca attaaatgtg tgagtccata ctgatataaa tgtttaaata   11640
aataaataag gagataagag acagatattc tttacaaaag cattctagat aatacacata   11700
ggtactctcc cttaaggagg tggagcttat tgcctgccct ccttgtgagt gggttagact   11760
taataattca tttccaaaga gtaggtagga aaggggaaa accatgcaga aacctggcaa    11820
agccaacatt aatcaaatga tcaaggctaa cgtaaccagg gatgatacat attaccatgt   11880
gacaatacga cacttcacct ctttggtgtc tccctaaacc ccatacctaa agttcagact   11940
cttaaactat gagaaaaaca gcagacaaag tcagcttagt ggacattctg taatacctgg   12000
tcctcaagac tatcaaggcc atgacaaaca aggaaagact aagaaactat cacggaccag   12060
aagagactgg gaaaacatga caattaatgc agtgtgtgta ggatgtggac tggattctag   12120
aacacaaaga cgatattaat gaacaaactg gtaaaattcg aataaagtct gtaatttagt   12180
tagtagtaat atgccaatgt cagtttcgac aaatctttgc aacttttctg taattctaga   12240
actatcccca aataaaaatg cattaaaaaa aaaaaacaa aaaaaccaaa cacttgcatt    12300
aggaaaggat tgcatatact ggcaaaactt cagccagcaa gtgcccctga cctcggcgaa   12360
tgtccccaca tgaagagata tctcagacgg acttgtggca cccagtgggt ctgcacggac   12420
atcagcatcc tgactgtgtt gctccagcac tccaaaatct ggcttcacca tctcacagag   12480
ctggggagaa cttgaaggaa gggcctagtg aaggacagca gacgggtgat ccttgcccaa   12540
gcgccctgac caccctgaaa ttctgtccca gtaaagaaag accaagcatg gccagtctgg   12600
ggcacatgaa gcttgtgttc ccaggcggat aggtggccag gaacctctga gggacatctg   12660
cagtgacctg agctcgtcat gaggtgacca tcataggtat gaccttgggg cctcatgact   12720
ggagtggctc catggtggct aactgacagc tggagctcag gacttggttc ctcttagcca   12780
agagcagtta ccggatgtga atcctgtttg gcatagagtt ctgactggaa ccagaaaact   12840
tttgtcttac cttcagctct gggctccagc aaacctcctt ctgtcacaga gactcagaga   12900
aaaggcccag caggtaccct cagcaagcaa gcattaagta caaatgttct cggttatcaa   12960
ctccacacaa atgagatatt cctttcttcc atctaacaaa cattcgtgaa gtccctgcta   13020
cattttggcc cctctcctca tcctggggat gcagcagcac acacggcaga gccctcactc   13080
tcctggagct cattatgcgt ctaagggga gggaagacg atcaacaaat gacaaggagt      13140
gctatggagg gagacgaagt gggagagaac agcatgtgct gctgggggag gtgggggcc    13200
```

```
ctgacataag ggatcaagca tgtgggaaag tctctctgat aaggcggcgt ttgaggagcc    13260
ctgagcaatt atgccatgaa tcatatgctt gttaggaaga gcctcctggg cagtggcaac    13320
agctcgtgca aaggccctgg cgtggtcaag aagcagaaag agacccgtg  agggaggaga    13380 gaatggcagg agtagatgca gaaaagcagc aggtcttcgg tggggcgctg gttacgagca    13440
gcacacgacg gtcccaggcc acagaagcag tctggctttt cctcggattg tatctccaga    13500
gagataatgg tgtgaatact atgaacagta tagagaaact caaggaaga  agccagttgg    13560 ggggaaatga tatttctgtg tctgcctgag gtgctattaa agtgaccagg tgagggcgc     13620 ctgggtggcg cagtcggtta agcgtccgac ttcagccagg tcacgatctc gcggtccgtg    13680
agttcgagcc ccgcgtcagg ctctgggctg atggctcgga gcctggagcc tgtttccgat    13740
tttgtgtctc cctctctttc tgcccctccc ctgctcatgc tctgtctctc tctgtcccaa    13800
aaataaataa acattgaaaa aaaaatttta aaaaaaaaaa aaagaagaa  aaaaaaaat     13860 aaagtgacca ggtgacagga ctcggtcaag agacgactag aacctgggca ccagcatgta    13920
ggggagggtt cagggctcca gaatcagatt caggagactg gctcaaggga ggccactgag    13980
caggtcaagg acacagatta tgacgaaggc agggcaggag ccaccagaga ccggcctcct    14040
tttggtactt gctagctgtg agtccactag ctaagcactg ggtttcctga aaaatccgta    14100
agttgagacc agaccatctt caaggtcaca tgaaagacag gctgacattg cccatcatt    14160 cgggaggcct gacttgggag actctcttgc ccctttcccc agtcaaccta gaaaatttca    14220
gttctgaaat tactggtgtc agctgacact tggacagagc cctcaagacg ggaaggga     14280 gccaaggtag cgtcatctgt tgactcgggg acttaggatc ctgcccacac atacatctcc    14340
tccctccaca gcccccaggc agttctgaga agcagcccag agaggcctgg cggtgcctcc    14400
tggaaaagga tgttagacgc agccctccca ccctgcccta ctgttgcagc cacagcaggt    14460 ataaagggt  tccaggctgg ggagggagca cctgccactg catcatgaag ggggctcgtg    14520
ttctcgtgct tctctgggct gccttgctct tgatctgggg tggaagtagg tgtctgggac    14580
atgagtgtct ggggacacag attctccagg ggttctaaca ccttcccagg gcacttctga    14640
gcatggcggg aaggggaagg gaagaatgtg tcctgatgaa ggtctttcaa aagggagggt    14700
cagcttgtct ttgtgttcca gattgtgaaa tttgcccagc cgtgaagagg gatgttgacc    14760
tattcctgac gggaaccct  gacaaatatg ttgagcaagt ggcacaatac aatgcacgac    14820
ctgtagtatt ggcaaatgcc agaaacctga agaactgcgt tgatgcaaaa atgacagaag    14880
aggataagga gaatgctctc agcgtgctgg tgggtctagc tctgtgtctg tgcctctgac    14940
gcctgtctgg ggggtctgct cagggcagtg caggaggggg gttgctcatg tttgttctcc    15000
accatggccc ttccctggga atctgggagg agaaagacgc catggctggg gaagtagagg    15060
ggatcatgtg gggaagactc agcctacccc tcaagctttg gggctggccc aggctgctca    15120
acgctgcttg gccaccggct tgggggtctg caggccctcc tgtgtccctg gcatcacttg    15180
gcctcagtgt caggccctca gctctggcct tcctgactcc agcctctcca gcacgtgaga    15240
ctggatcttc aaactgtttg cactaggtgc ttcctatctc caaacgtcag ttccttttct    15300
cttaactcct caagttccat attccacccc cccccaaa  aaaaacctca tctgtcgtca    15360
ttccctgggt cccagaggcc attctgtgcc tcaaatactg agagagagga ggaggggagg    15420 ggagggggaga ggagaggaga ggagaggaga ggagaggaga ggagaggaga ggagaggaga    15480
ggagaggaga ggagaggcag cttccaaaaa gttctcctgc cctgcccagg cctgggatgc    15540
ctgagtggag aattccagtg aatcctctct ctgctgtccc aaagtaggaa caagctactg    15600
```

```
cttcagcaac aagtgttcaa aggacagaag aaggaagcag gctggaccag ctcattcctg   15660
gagtctccag atgcccacag gtgcatctgg agccctgcca ggaccttctt gccagcgtct   15720
ttctaaccaa gtctaccact tctatccgag actgccctcc atcccatcat agtcacccct   15780
cttcttcact ctgtttcatt ggaggaagct tctaggcaca ccctgggatt ctcttgttgt   15840
gcagtagatt gggaagaacc accttggcct gctcagatcc agaagccacc ctccaaacaa   15900
gcctgcaggc tcctccccac aaagtgtcca gtgcgtgctc agtagtgttt gtccgttctc   15960
acgtacccct caaggtctca ccaggtctcc tgactttctc tttgcaggac aaaatataca   16020
caagtcctct gtgttaatgg agccatcact gccaggagcc ctaaggaagc cactgaactg   16080
attactaagt agtctcagca gcctgccatg tccaggtgtc ttactagagg attccagcaa   16140
taaaagcctt gcaattcatg gagagtgctt gctccttggg ctgggcttgg ggggggggt   16200 ggaggggtgt tgcagcaggg ggaccaccag tgtgccttcc aaccgtggct agatttgaat   16260
gcagtcagat gtccttcctc ccctgaatcc cagaggtgag gggaggggtg atgaccatta   16320
gcacaggtgg catgtctgag cacttccgtg gaccaggacc cacacctcac atgcattatc   16380
taccaaattt cagcctccca gtgacctcaa gagacgggga taatcatccc agtcttacaa   16440
gcgaggagac tggggctcgg agaggtaaag tgtctgccaa agattacagg ctcccgggcg   16500
tcaggacctg ctgcatctgt gcacccactg ccagagacgg ctcagctcac cgtgtggctg   16560
tgcatgtgtt agtccttctc tgggcctctg attccacct agaaaatgga aatacctccc   16620
ctctccaggg cctctttggt ggggccacag aaaatcatgg gtgagaaaca gcccctgtcc   16680
caagcacctg gatggagaga aagaacaagg gtcaaggtgc gagtggtgaa ccccgtcctc   16740
ctgcacctca gtttacccta gtgccgacca cccaactgtg gattcggctg ccccccttgta   16800 cttaacacac tacaagttgg gtctaatgct cagagtggat gtccagggtc ctggagctgc   16860
agaactcctc ttgtggctct gttctatggc catgattccg gaggcttctc aggccctgct   16920
gccctcatct gtctcctctt ggccaggatc cttgcctcct ctcttaacgc ttccatcccc   16980
accacctgag cactccccca gaaaagagtc tgctgaactt acactgcagg gcttccccca   17040
ggaggggtat ctctgtgatc attttggtga agaggctgag gaaaggttcc cagagggat   17100 ctctctctct ctctctctct ctctctctgt ggagcacgtc atgggacag gagaaggaag   17160 gccaccttgc ccagagtgag acctggctct tggcctatgg cccaccactc tgaccccag   17220 ggtctggccg gaggctactt ctgaaatgga gcactgcccc catggtagca aggggagtcc   17280
agaggtcata agcaggttgt ggggcagaga cccttctcat caccctccca tatgtgaccc   17340
agggtgtata ttccaccact ccccaccat acatactgaa aagttcttgg gcttacagaa   17400
ggaaagctgt cacccagatg agtgggccag gtcttccaat gtcatagatg aagactcacc   17460
ctggtccaca gcaagtgtag ggagtgaggg gcaccccacc caaaggtgag aaggtgatga   17520
gcaacgggca gtttgtcctc accaagacac aaccagcccc ccaactgctg ctagactcgc   17580
acagaactcc ctggggactg atggcaccta tgacatctgg acgctttctg tgtaatccct   17640
cccctctggc tgcgttccaa acagccagat ggctgtctga catccaaacc tcagatagct   17700
gaaaggtaaa tatcaggaac ataagggtga cgcttttgat ctctgattca cacatgagat   17760
cataaaagcc ccgccccact tccccgtggt ctgacctaaa ttcgcccaaa acggtggtgg   17820
ataatcccct cttggagaca tcttccctct tcaaacactt gcatctttct tcactgttcg   17880
ctggttttct ccaccacctg ggagcttgcg gaactctgtt cagctccctc tgcgtgtgtg   17940
aagctgatca tgcctacagg gcaaccctga acaattcgg accccagcct cctcaacttc   18000
```

```
tggcgggtca gttctgaagt gaattccaca cggtctctga taggtgccca gtggtcttga    18060
gtcccagttg gccaatcttg cggcttttct cattttcctg tttcactgga gcaccctgag    18120
gtcgcttccc aaataaagtg cctgccctca tgtccctgtg tctgggtctt ctttgctggg    18180
aactcaaact gacacgatga ccgacatcca tccgcctgat caagaaggaa aggcgacgaa    18240
gtacagtaga agacatttgc cgaaggcaag aagacaggac tgttagagcc cgaggcacat    18300
cttacagact gaagccatga ggggtgagcc catactacat tctttcaaga gagacacaga    18360
aggaatcaga ataaatcagc aagctatcta acccattttg gtctagttgc ctgggggga    18420
aaaaataaag caaggcctaa gattactggg aagccccaga ctaagagaga ccctggaagg    18480
agtccaggag gaacaaggca agatcaccaa ggtccaggga aactgtgccc acatgcagca    18540
tggtgtacaa tgtgctccct gcataagcac aggcttacga aacactccac cgctcagcaa    18600
atgccttgaa gtgggaaaaa catagtgaaa aataaatctc tcattctctt ttcctcctca    18660
aaggcccacg aaaaagacag taaaacaatt taaaagcata agcccacatg gaatacattg    18720
ctctttgtat ttaaccacag gaacaagagt tttcatttcc tcttgaacag tttggggata    18780
attcagtact atgcagataa taacaaagta tgagcaagcc taacctaaaa aatgtataaa    18840
aatatatact ttgtaaaaaa aagaaagttt attttgttcc aagaatgtaa acataactta    18900
gcattacaaa aatacagaat tccctgcctt aagagactaa aagagaaaaa aaacaaatgg    18960
tcatctaaac tggtgcagaa aaagtttcat aatactggac acttacgatt ttcaaaaatt    19020
aacagaatgg gaataaaaga ggttttcatg agaacgataa agtgcattta taaaaaaaac    19080
taaaggagca ctaaggaatc tactcctgaa atcattgttg cactatatgc taatttggat    19140
gtaaattaaa aaaaaaaaaa actaaatggg tgatgggcat taaggagggc acttgttatg    19200
atgaacactg ggtgttatat gtaagtgatg aatctctaaa ttctactcct gacaccaata    19260
ttacgctata tgttaactaa ctaggattta aattaaaatg tgaaagaaaa attaataaat    19320
aaatttaaat gtttttaaag aaaactaaaa aaaattttta aactatgaca aacttcatac    19380
ttgatggtaa gatattacaa gaggtccact taaaataaga aataaggtaa gatgcttatc    19440
aaggtatcac ttctactata aacattatag tatacttact aaccaattca ggaagaaaag    19500
aaagtatgat attaatgaag tagaaaacag ataagaaatt aagaatatcg gggcacctgg    19560
gtggctcagt cagttaagtg tccaacttca gctcaggtca tgatcttaac agttcgtggg    19620
ttcaagcccc acatcgggct ctgtgctggc agctcagagc ctggagcctg cttcggattc    19680
tgtgtctccc tctctctctg ccccttgccc actctctctc tctctctctc tctctctctc    19740
aaaaattaaa gaacattaaa aataaatttt tttaaaaatt aagaatatca ataacaccaa    19800
aaacagtttt tttgaaaaat caattaaagt tgataaacct gtaccactga tcaagaagaa    19860
aagaagacac aaaattaccaa tcagaaattg aaaaggggat ggctttaaag aattaaactt    19920
ttaattaaaa ctttgcacgt agttagtgtg cccggatggc tccgtcggtt gagcaaccga    19980
ctcttggttt cagctcaggt tatgatccca aggtcgtggg atcaagcccc acactaagaa    20040
atgtatagaa gtgtttacct gaaactaata caatattgta tgttacttat acttgaatta    20100
attaagataa taccaatta ttgcttcttg gcccggtata ccccttaaga ggacatctcc    20160
tggcacttcc aagaagttct cggggtgccc agagtgcaaa ctaatgcccc atccaggcaa    20220
ccccactcag catagccccg tctaggaatt gccaggggat tgccctgtta ccttccaagc    20280
agctgaatat tcttttgcat taatccagtt acttcaggcc cttacatagt tgtggccact    20340
cactgctgat tttgcccctg ctaataagtc atacttatca gtctgggtcc ggtcaggaga    20400
```

```
caggaatcac accagtaatt tgaacatcta tatatgtagg atgttttcac tgtgtcccat    20460
gtatttccta catattttc  tatattttag attcttccat ctttctgttt tattctatat    20520
attttccttt gatcgaaatt accacttaat tttctcaaca gctgcaccta atctgctcct    20580
taatatattg ctcgaatact catcttgttt ctcagctcca gaatgtctat tttgttcttt    20640
ttattaagaa aaaaaatgag attttctttc tttttttttt taatgtttgt ttttgaaaga    20700
gagagctgag gagggcaga  gagagaggga gagaaagaat cccaggcatg ctccacgctg    20760
tcagcgctga gcctgacatg ggcttgatc  ccacgaacgg ttgagatcat gacctgaact    20820
gaaatcaaga gacgcttaac cgactgagcc acccaggtgc tccaaaaata cattttttt    20880 aaaaggaaaa aaagaacgat gcagcaaagt cagtactaag aagaaaatac aatgcaatcc    20940
aggcctatct caagaaacaa gaaaaatccc aaatacaaaa tctaatggcc tacctaaagg    21000
aactagaagc agaacagcaa acacaccgca acccagcag  aagaagagaa ataataaaga    21060
taagagcata aataaacaat atagaatcaa aaaaaaaaaa aaacccagt  agaacagatc    21120 aattaaacca agagttggtt ttttgaaaaa ataaacaaaa ttgataaacc tctagccagg    21180
cttctcaaaa agaaaagaga gaggacccaa atagataaaa tcatggatga aaatggaatt    21240
attacaacca atccctcaga aatacaagca attatcaggg atgtacaatg aaaaattgta    21300
tgccaacaaa ctggacaacc tggaagaaat ggacaaattc ctaaacaccc acacactcaa    21360
aagggaagaa atcaaaaatt tgaacagacc cataactagt gaagaaattg aatcagttat    21420
caaaaatctc ccaacaaata agagtcctgg accagaaggc ttccctgggg aattctacca    21480
gacatttaaa gccgagttaa tacctatcct tctcaagctg ttccaaaaaa tagaaaggga    21540
aggaaaactt ccagactcat tctatgaagc cagcattact ttgattccca aaccagacag    21600
agacccagca aaaaaaaag  agaactacag gccaatatcc ctgatgaata tggatgcaaa    21660
aattctcaac aagatactag caaatcaaat tcagcagtat ataaaagaa ttattcacta    21720 tgatcaagtg ggattcattc ctgggctgca ggctggttca atattcacaa atcaatcaat    21780
gtgatacatc acattaataa aagaaaagat aagaaccata tgatcctgtc aatagatgca    21840
gaaaaagcat ttgacaaaat tcagcatcct ttcttaataa aaaccctcaa gaaagtcagg    21900
atagaaggaa catacttaaa catcatacaa tccatttat                           21939
```

<210> SEQ ID NO 8
<211> LENGTH: 6
<212> TYPE: PRT
<213> ORGANISM: Felis catus

<400> SEQUENCE: 8

Ile Ala Ile Asn Glu Tyr
1               5

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgacagaag aggataagga gaatgc                                          26

<210> SEQ ID NO 10
<211> LENGTH: 25
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 10
gtaggccatt agattttgta tttgg                                        25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggatcttcaa actgtttgca ctagg                                        25

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttctttttt tccttttaaa aaatgtg                                      27

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agtgtttctg atactaaaca aagtccag                                     28

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttctttaca cctaaagctg gaatcc                                       26

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcatttctct ggaattaagt ggc                                          23

<210> SEQ ID NO 16
<211> LENGTH: 26
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 16
gttctttaca cctaaagctg gaatcc                                         26

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgactgtgcc ttctagttgc c                                              21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttgtgtagcg ccaagtgcc                                                 19

<210> SEQ ID NO 19
<211> LENGTH: 92
<212> TYPE: PRT
<213> ORGANISM: Felis catus
<220> FEATURE:
<221> NAME/KEY: mat_peptide
<222> LOCATION: (23)..(92)

<400> SEQUENCE: 19

Met Lys Gly Ala Cys Val Leu Val Leu Leu Trp Ala Ala Leu Leu Leu
        -20                 -15                 -10

Ile Ser Gly Gly Asn Cys Glu Ile Cys Pro Ala Val Lys Arg Asp Val
     -5                  -1  1               5                  10

Asp Leu Phe Leu Thr Gly Thr Pro Asp Glu Tyr Val Glu Gln Val Ala
             15                  20                  25

Gln Tyr Asn Ala Leu Pro Val Val Leu Glu Asn Ala Arg Ile Leu Lys
             30                  35                  40

Asn Cys Val Asp Ala Lys Met Thr Glu Glu Asp Lys Glu Asn Ala Leu
             45                  50                  55

Ser Val Leu Asp Lys Ile Tyr Thr Ser Pro Leu Cys
     60                  65                  70

<210> SEQ ID NO 20
<211> LENGTH: 88
<212> TYPE: PRT
<213> ORGANISM: Felis catus
<220> FEATURE:
<221> NAME/KEY: MOD_RES
<222> LOCATION: (31)..(31)
<223> OTHER INFORMATION: Leu or Lys
<220> FEATURE:
<221> NAME/KEY: MOD_RES
<222> LOCATION: (60)..(60)
<223> OTHER INFORMATION: Val or Leu
<220> FEATURE:
<221> NAME/KEY: mat_peptide
<222> LOCATION: (19)..(88)

<400> SEQUENCE: 20

```
Met Leu Asp Ala Ala Leu Pro Pro Cys Pro Thr Val Ala Ala Thr Ala
            -15             -10                 -5

Asp Cys Glu Ile Cys Pro Ala Val Lys Arg Asp Val Asp Leu Phe Leu
 -1   1           5                      10

Thr Gly Thr Pro Asp Glu Tyr Val Glu Gln Val Ala Gln Tyr Asn Ala
 15              20              25                       30

Xaa Pro Val Val Leu Glu Asn Ala Arg Ile Leu Lys Asn Cys Val Asp
                 35              40                  45

Ala Lys Met Thr Glu Glu Asp Lys Glu Asn Ala Leu Ser Xaa Leu Asp
             50              55                      60

Lys Ile Tyr Thr Ser Pro Leu Cys
         65              70

<210> SEQ ID NO 21
<211> LENGTH: 92
<212> TYPE: PRT
<213> ORGANISM: Felis catus
<220> FEATURE:
<221> NAME/KEY: MOD_RES
<222> LOCATION: (-18)..(-18)
<223> OTHER INFORMATION: Cys or Arg
<220> FEATURE:
<221> NAME/KEY: MOD_RES
<222> LOCATION: (-5)..(-5)
<223> OTHER INFORMATION: Ser or Trp
<220> FEATURE:
<221> NAME/KEY: MOD_RES
<222> LOCATION: (31)..(31)
<223> OTHER INFORMATION: Leu or Lys
<220> FEATURE:
<221> NAME/KEY: MOD_RES
<222> LOCATION: (60)..(60)
<223> OTHER INFORMATION: Val or Leu
<220> FEATURE:
<221> NAME/KEY: mat_peptide
<222> LOCATION: (23)..(92)

<400> SEQUENCE: 21

Met Lys Gly Ala Xaa Val Leu Val Leu Leu Trp Ala Ala Leu Leu Leu
        -20             -15              -10

Ile Xaa Gly Gly Asn Cys Glu Ile Cys Pro Ala Val Lys Arg Asp Val
 -5              -1   1           5                       10

Asp Leu Phe Leu Thr Gly Thr Pro Asp Glu Tyr Val Glu Gln Val Ala
             15              20                       25

Gln Tyr Asn Ala Xaa Pro Val Val Leu Glu Asn Ala Arg Ile Leu Lys
             30              35                  40

Asn Cys Val Asp Ala Lys Met Thr Glu Glu Asp Lys Glu Asn Ala Leu
         45              50              55

Ser Xaa Leu Asp Lys Ile Tyr Thr Ser Pro Leu Cys
 60              65              70
```

NUCLEIC ACID SEQUENCES AND HOMOLOGOUS RECOMBINATION VECTORS FOR DISTRUPTION OF A FEL D I GENE

FIELD OF THE INVENTION

This invention relates to the production of transgenic animals wherein a recognized gene sequence, coding for an identified allergen, is inactivated. More particularly, the invention relates to transgenic cats wherein the gene sequences, coding for the major cat allergen Fel d I, have been disrupted.

BACKGROUND OF THE INVENTION

Approximately 6 million Americans are allergic to cats, and although many persons allergic to cats do not have cats in their own homes, almost one third do. It has been suggested that 28% of homes in the United States have at least one cat (which equals at least 50 million cats). Patients allergic to cats often report a rapid onset of asthma and rhinitis upon entering a house with a cat. When tested, almost all of these patients will show a positive immediate hypersensitivity skin test to extracts of cat dander and will have serum IgE antibodies against cat allergens (Luczynska, *JACI*, August 1989).

To date, most treatments to cat sensitivity have centered around avoidance and immunotherapy. Avoidance can mean considerable alterations in ones living environment and daily routines. For example, to avoid excessive exposure to indoor allergens it is recommended that carpets be removed from floors, bedding be covered with special sheets, air conditioners be cleaned regularly, and air be filtered with costly air filters. The time, effort and expense often makes this type of treatment unappealing to allergy sufferers.

Immunization can be an effective treatment for allergies. Unfortunately, the expense of regular allergy shots, the time involved to receive treatment, and the variability of effectiveness are considerable deterrents for some patients. Furthermore, there is risk that a patient may have a severe reaction to the immunization and can even go into anaphylactic shock.

SUMMARY OF THE INVENTION

This invention is directed to a new alternative to traditional treatments for allergies. Rather than recommending avoidance or immunotherapy, this invention eliminates the allergen at its source. In the case of the cat, sensitivity has been attributed to one major cat allergen (Fel d I) (Ohman, *JACI*, 1972). Using, newly developed gene targeting techniques it is possible to "knock-out" the Fel d I genes in an embryonic cell, i.e., Embryonic Stem (ES) Cells. These modified ES cells can then be introduced into a developing blastomere. During normal embryonic development the ES cells will then be incorporated into part of the germ line (Capecchi, *Science*, June 1989), (Robbins, *Circulation Research*, July 1993).

One embodiment of the invention is directed to an isolated nucleic acid comprising at least part of the sequence depicted in SEQ ID NO. 7. In another embodiment, the "part" comprises at least about 5, at least about 10, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 consecutive nucleotides of SEQ ID NO. 7.

Another embodiment of the invention is directed to a homologous recombination vector, comprising: (1) a first homology arm, (2) a desired polynucleotide, and (3) a second homology arm, wherein the desired polynucleotide is positioned between the first and second homology arms, and wherein each of the first and second homology arms comprises at least about a 1 kb sequence of SEQ ID NO. 7. In another embodiment, the homologous recombination vector comprises at least about 5, at least about 10, at least about 15, at least about 20, at least about 25, at least about 30, at least about 35, at least about 40, at least about 45, or at least about 50 consecutive amino acids of SEQ ID NO. 7.

In one embodiment, the first homology arm comprises any sequence between nucleotide 1 to about nucleotide 8,800 of SEQ ID NO. 7. In another embodiment, the first homology arm comprises any sequence between nucleotide 1 to about nucleotide 10,000 of SEQ ID NO. 7. In a further embodiment, the first homology arm comprises any sequence between nucleotide 1 to about nucleotide 10,800 of SEQ ID NO. 7. In another embodiment, the first homology arm comprises any sequence between nucleotide 1 to about nucleotide 14,800 of SEQ ID NO. 7. In another embodiment, the "any sequence" comprises at least about 5, at least about 10, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 consecutive nucleotides of SEQ ID NO. 7.

In one embodiment, the second homology arm comprises any sequence between about nucleotide 16,000 to nucleotide 22,182 of SEQ ID NO. 7. In one embodiment, the second homology arm comprises any sequence between about nucleotide 14,700 to nucleotide 22,182 of SEQ ID NO. 7. In another embodiment, the second homology arm comprises any sequence between about nucleotide 10,800 to nucleotide 22,182 of SEQ ID NO. 7. In another embodiment, the "any sequence" comprises at least about 5, at least about 10, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 consecutive nucleotides of SEQ ID NO. 7.

In one embodiment, either or both of the homology arms comprises a SEQ ID NO. 7 sequence that has a length selected from the group consisting of about 1 kb long, about 2 kb long, about 3 kb long, about 4 kb long, about 5 kb long, about 6 kb long, about 7 kb long, about 8 kb long, about 9 kb long, and about 10 kb long.

In another embodiment the desired polynucleotide is a selectable marker.

Another aspect of the present invention is a method for disrupting a target Fel d I sequence in a feline cell genome, comprising introducing the homologous recombination vector of claim 1 into a feline cell, wherein: (a) the homology arms of the vector function to recombine with the cell genome and (b) the desired polynucleotide integrates into the cell genome at the target sequence site thereby disrupting the target sequence.

Another aspect of the present invention is a feline cell comprising any of the desired polynucleotides described herein. In one embodiment, a desired polynucleotide is integrated into the feline cell genome. In one embodiment, a feline cell containing a desired polynucleotide does not express Fel d I RNA or protein. In another embodiment, a feline cell that has been exposed to a homologous recombination vector as described herein does not produce a Fel d I protein, or produces an inactivated Fel d I protein. Thus, in one embodiment, a cat that is produced from feline cat cells that do not express the Fel d I protein is a cat that does not produce a Fel d I allergen. The present invention contemplates, therefore, a cat which does not produce a Fel d I protein because cells of the cat have been manipulated according to the present invention to have lowered or no expression of the Fel d I protein. A cat that is so produced therefore has a different Fel d I protein expression phenotype compared to a cat that contains cells that have not been subjected to the homologous recombination vectors described herein. Thus, a cat of the present invention has different or abnormal Fel d I expression traits compared to a non-transgenic cat that has not been produced from cells that have not been manipulated according to the present invention.

The resulting chimeric offspring will be heterozygous for the inactive Fel d I gene. When cross-bred with another heterozygous cat, one fourth of the progeny will be homozygous to the inactive Fel d I gene. These homozygous cats are major allergen free and are a revolutionary alternative to immunotherapy for allergic cat owners (FIG. 1).

This invention is applicable to all animals in which a specific allergen can be identified and in which the disruption of the gene sequence coding for the particular allergen causes no harm to the animal.

This invention is based on the production of transgenic animals in which the gene sequence for a particularly allergen has been disrupted by a specialized construct rendering the gene inactive. In the preferred embodiment the altered gene will be transmissible to the offspring.

Embryonic stem cells are pluripotent cells derived from the inner cell mass of the blastocyst. These cells retain the ability to differentiate into any tissue type in the developing body. A change in the genomic sequence of an ES cell will be passed on to all other cells derived directly from the altered ES cell line.

The Fel d I gene coding for the major cat allergen is disrupted or "knocked-out" in the embryonic stem cell of a cat. This is accomplished by inserting into or replacing part of the functional gene with a new sequence of genomic DNA, rendering the gene inactive. The modified ES cell can then be introduced into a developing blastomere by one of several recognized techniques and then implanted into a pseudopregnant foster cat. During normal embryonic development, cells derived from the altered ES cell are incorporated in part of the germ line and somatic tissue.

The resulting chimeric offspring are heterozygous for the inactivated Fel d I gene. When cross-bred with another heterozygous cat, approximately one fourth of the progeny will be homozygous for the inactive Fel d I gene. These cats are major cat allergen free. The altered gene and subsequent phenotype is transmissible to future offspring.

The invention provides an isolated polynucleotide sequence encoding a disrupted Fel d I gene. In accordance with the invention, such a sequence can be disrupted by sequence replacement, sequence insertion, or deletion of all or a part of the Fel d I gene. In further embodiments of the invention, a nucleotide sequence encoding a selectable marker is inserted into the Fel d I gene or used to replace all or part of the Fel d I gene. An example of such a selectable marker gene is a gene that confers neomycin resistance.

In another embodiment of the invention, there is provided a recombinant polynucleotide vector comprising all or part of a disrupted Fel d I gene. In yet another aspect of the invention, there is provided an embryonic cat stem cell comprising a disrupted Fel d I gene and an embryonic cat stem cell comprising a vector which in turn comprises a disrupted Fel d I gene.

In yet another embodiment, the present invention provides a transgenic cat comprising a disrupted Fel d I gene. The Fel d I gene of the somatic cells, the germ, line cells, or both the somatic and germ line cells of such a transgenic cat may be disrupted. In accordance with the invention, there is provided a transgenic cat which is heterozygous for the disrupted Fel d I allergen gene. There also is provided a transgenic cat which is homozygous for the disrupted Fel d I gene. Transgenic cats comprising a disrupted Fel d I gene are provided that are fertile and capable of transmitting the disrupted Fel d I gene to its offspring are also provided.

The present invention also provides a first method for producing a transgenic cat comprising a disrupted Fel d I gene, comprising the steps of:
(a) introducing a cat stem cell comprising a disrupted Fel d I gene into a cat embryo;
(b) transplanting the embryo into a pseudopregnant cat; and
(c) allowing the cat embryo to mature into a cat.

Transgenic cats produced in accordance with this method can be heterozygous or homozygous for the disrupted Fel d I gene. Homozygous transgenic cats will not produce the Fel d I cat allergen.

Finally, in another embodiment of the present invention, there is provided a second method for producing a transgenic cat comprising a disrupted Fel d I gene, wherein the cat does not produce the cat allergen Fel d I, and wherein the cat is homozygous for the disrupted Fel d I gene, comprising the steps of:
(a) producing a first heterozygous transgenic cat according to the first method described above;
(b) producing a second heterozygous transgenic cat according to the first method described above, wherein the second cat is not the same sex as the first cat;
(c) breeding the first and second cats; and
(d) selecting transgenic cats which are homozygous for the disrupted Fel d I gene and do not produce Fel d I antigen.

Both the foregoing general description and the following brief description of the drawings and the detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 2 shows the nucleotide sequence of chain 1 (Ch 1) of the Fel d I gene in a cat. Ch 1 is composed of a mature protein subunit of 70 aa. Sequencing of the gene encoding for Ch 1 demonstrates that there are two alternative Ch 1 leader sequences with the leader B exon separated from the start on the leader A exon by an intron of 46 bp. The junction of leader B (exon 1) or leader A (exon 2) with exon 3 leads to alternative codons that encode either Asp (leader B) or Asn (leader A). These junctions (exon 1/3 and exon 2/3) are positioned 2 aa from the N terminus of the mature Ch 1, which starts with $Glu^1$. The structural gene is comprised of only two exons, 3 and 4, that encode the mature protein.

FIG. 3 shows the nucleotide sequence of chain 2 (Ch 2) of the Fel d I gene in a cat. Ch 2 is composed of a mature protein subunit of 92 aa. The leader sequence and the first 3 aa of the mature protein are encoded by exon 1 (61 nucleotides (nt): 20 aa). The bulk of the mature protein is encoded by exons 2 and 3 (aa 4-64 and 65-90, respectively). The first 18 nt of exon 3 of Griffith's published sequence encode the residues, IAINEY (aa 65-70)(Expression and Genomic Structure of the Genes Encoding FdI, the Major Allergen from the Domestic Cat, *Gene* (1992)), rather than Morgenstern's published sequence, TTISSSKD, suggesting that Ch 2 has two forms (Morgenstern, et al., *Proc. Nat'l. Acad. Sci. USA,* 88:9690 (1991)).

FIG. 4. depicts a schematic for a sequence replacement vector. Sequence replacement vectors are designed such that upon linearization, the vector sequences remain collinear with the endogenous sequences. Following homologous pairing between vector and genomic sequences, a recombination event replaces the genomic sequences with the vector sequences containing the neo$^r$ gene. A strp$^s$ gene can be place outside of the homologous coding region of the replacement vector to make future screening of ES cell colonies easier. Open boxes indicate introns; closed boxes indicate exons; the crosshatched box indicates the neo$^r$ gene.

DETAILED DESCRIPTION OF THE INVENTION

I. Transgenics

Figure 1:
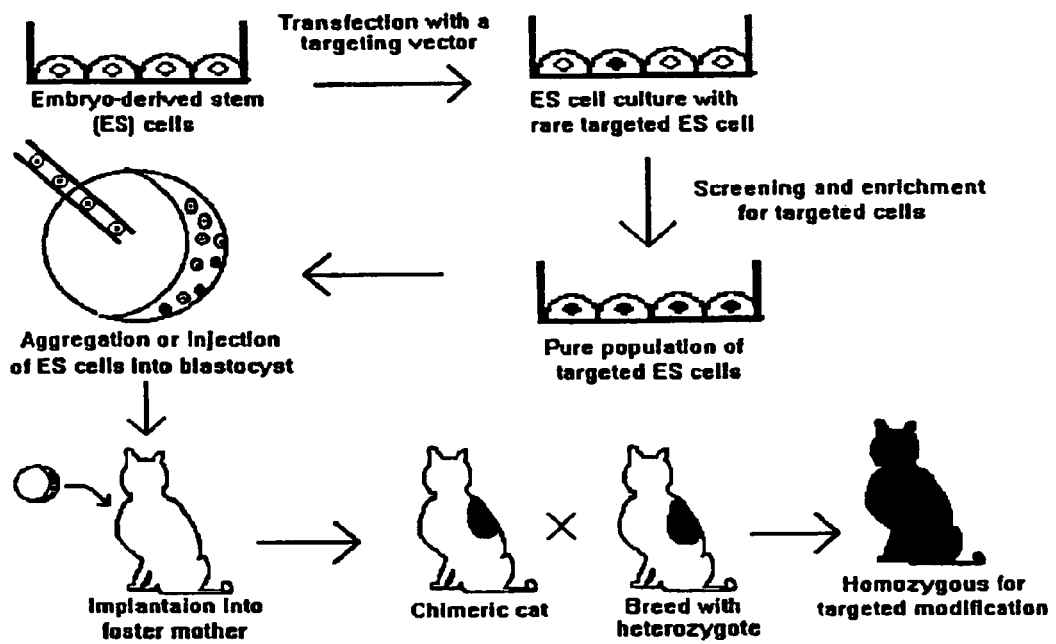
FIG. 1 is a schematic summary of the generation of cat germ line chimeras from embryo-derived stem cells containing a targeted gene disruption.

While this disclosure pertains to transgenic cats it is not limited to cats. The invention pertains to all animals in which a gene coding for an allergenic protein can be identified and inactivated without causing harm to the animal. The term "animal" is used herein to include all vertebrate animals, except humans. It also includes an individual animal in all stages of development, including embryonic and fetal stages. A transgenic "animal" is any animal containing one or more cells bearing genetic information received, directly or indirectly, by deliberate genetic manipulation at a subcellular level, such as by microinjection, infection with recombinant virus, or electroporation. The genetic manipulation may be directed directly at the chromosome or it may be directed towards extrachromosomally replicating DNA. A "transgenic animal" refers to an animal in which the genetic information was introduced into a germ line cell, thereby conferring the ability to transfer the information to offspring. If such offspring in fact possess some or all of that information then they, too, are transgenic animals.

The following is presented by way of example and is not to be construed as a limitation on the scope of the invention.

II. The Embryonic Stem Cell

The key to the production of allergy free cats is the successful incorporation of new DNA into the ES cell. The generation of chimeras between embryonic stem (ES) cell lines or clones and embryos is an essential step in these processes, which when successful leads to the derivation of new strains of cats with an altered genome.

Most ES lines that are currently in use have an XY or male genotype. This has two advantages. The first is that male XY ES lines, when injected into female XX blastocysts, will tend to bias the development of the resulting chimera toward a male phenotype. In phenotypically male chimeras, only XY-bearing germ cells (i.e., those derived from the ES cells) will form functional gametes. XX primordial germ cells (i.e., those derived from the host blastocyst) will not form functional gametes and are lost. This will, therefore, favor the development of gametes derived from the ES cells. Second, a male chimera can produce more offspring over its reproductive life span than a female, so that even chimeras with a relatively low percentage contribution of the ES cells to the germ line can be detected.

The length of time that ES cells have spent in culture since their derivation can also affect their ability to make germ line chimeras. Chimeras that are the strongest and of the highest frequency are usually those derived with early passage clones (i.e., up to 10-15 passages); thereafter, it has been noted that the extent and frequency of chimerism may often, but not always, start to decline.

To generate germ line chimeras efficiently it is essential that the ES line be tested, prior to any manipulation or selection, for its capability of generating chimeras at a high frequency. The criterion is that more than 50% of the offspring born should be chimeric, with the majority of these being able to transmit the ES genotype through the germ line. It is also recommended to determine the karyotype of any subsequent clones isolated by selection, prior to injection into blastocysts, thereby avoiding any clones having aneuploid karyotypes that may not produce germ line chimeras. This procedure will result in considerable savings in time and effort and need only involve counting of the chromosomes, using the C-banding staining technique if the ES cell line used has already been assessed as to its ability to produce germ line chimeras. Any deviation from a mean number of chromosomes will almost inevitably result in weak chimeras being produced, with little possibility of the ES cells contributing to the germ line. The exception, however, is loss of the Y chromosome from a male ES line. Such clones can produce very good chimeras, resulting in germ line transmission by the females.

A. Derivation of Embryonic Stem Cells

The following procedures were adapted from the protocol described in Abbondanzo, Gadi, and Stewart, "Derivation of Embryonic Stem Cell Lines." Methods in Enzymology, 1993. Embryonic stem (ES) cells are the pluripotent derivatives of the inner cell mass (ICM) of the blastocyst. ES cells are derived directly from the ICM of blastocysts explanted in vitro. A variety of procedures have been employed to obtain ES cells, including using blastocysts that have undergone delayed implantation as well as culturing cells directly from ICMs isolated from blastocysts following immunosurgery. The derivation of embryonic stem cells is disclosed in full in Abbondanzo, Gadi, and Stewart, Derivation of Embryonic Stem Cell Lines, *Methods in Enzymology* (1993).

The in vitro growth of ES cells is dependent on the cytokine leukemia inhibitory factor (LIF). This protein is essential for maintaining the growth of ES cells in vitro since, in its absence, ES cells differentiate and eventually will cease to proliferate.

Leukemia inhibitory factor can be supplied to ES cells in different ways. Currently the best approach, and still the most effective one for long-term culture, is to grow the ES cells on a feeder layer of fibroblasts. The feeder layers synthesize and secrete LIF into the culture medium, and, in addition, an alternative form of LIF is also produced that remains closely associated with the extracellular matrix deposited by the fibroblasts. LIF is the only factor produced by the feeder layers that is essential for ES cell growth.

Embryonic stem cell lines can also be established and maintained from embryos in the absence of a feeder layer. Under these conditions the culture medium is supplemented with recombinant LIF, which is available from commercial suppliers (GIBCO-BRL, Grand Island, N.Y.; R and D Systems, Minneapolis, Minn.). It is also possible to use regular culture medium supplemented with medium "conditioned" by growing certain cell lines (see below) that secrete relatively large quantities of LIF into the culture medium. The medium can be collected and used at an appropriate dilution as a source of LIF.

B. Culture Requirements

To establish and culture ES cells, a laboratory equipped with standard tissue culture facilities is required, namely, a sterile/filtered air culture hood, a $37CO_2$-gassed incubator, and a tissue-culture microscope equipped with phase-contrast optics for viewing cells. In addition, a good stereo dissection microscope is required with ×40 magnification, along with a mouth-controlled pipette that is used for transferring blastocysts and for picking the ICMs or ES colonies. See (Abbondanzo et al., *Methods in Enzymology*, 1993)

C. Culture Media

The effective maintenance of ES cells requires that all culture media be made with very pure water. The Millipore (Bedford, Mass.) Five-bowl Milli-Q purification system provides water that is of satisfactory quality. A variety of different media have been used to culture embryos and ES cells: Dulbecco's modified Eagle's medium (DMEM), Glasgow modified Eagle's medium, and a DMEM/Ham's F12 mixture. Good results are obtained with DMEM with high glucose (4.5 g/liter), L-glutamine, and no sodium pyruvate. The medium is purchased in powdered form, although 1× to 10× concentrated liquid forms are available. It is made up according to the manufacturer's instructions and buffered with 2.2 g/liter sodium bicarbonate. It is supplemented with MEM nonessential amino acids to a final concentration of 0.1 mM [these can be obtained from GIBCO-BRL as a 100× (10 mM) solution]. In addition, L-glutamine to a final concentration of 2 mM is added together with 2-mercaptoethanol at a final concentration of 0.1 mM [a stock 0.1 M solution is made by adding 70 ul of the standard 14 M solution (Sigma, St. Louis, Mo.) to 10 ml of phosphate-buffered saline (PBS)]. Penicillin (50 IU/ml) and streptomycin (50 IU/ml) are also included in the final formulation, and 100× solutions can be obtained from GIBCO-BRL. This formulation is referred to as ES-DMEM. See (Abbondanzo et al., *Methods in Enzymology*, 1993)

D. Preparation of Feeder Layers

Embryonic stem cells are dependent on the cytokine LIF to maintain them as an undifferentiated proliferating population. The cytokine is usually supplied by growing the cells on mitotically inactive feeder layers of $G418^r$ fibroblasts that produce LIF. (Ramirez-Solis et al., *Methods in Enzymology*, 1993), (Robbins, *Circulation Research*, 1993). Recombinant LIF is commercially available but is expensive. ES cells have been derived from blastocyst cultures in the absence of feeders, but with the medium supplemented with recombinant LIF. However, the majority of these lines contain a significant percentage of aneuploid karyotypes, rendering them unsuitable for the generation of germ line chimeras. Only in a few instances have germ line chimeras been produced with ES cells established in feeder-free LIF-containing medium. As yet it is unclear as to whether feeders are providing, in addition to LIF, other factors that help to establish and maintain ES cells. Possibly, the matrix-associated form of LIF, along with the extracellular matrix deposited by the feeders, is more effective in maintaining ES cells than the soluble form alone. It has been found that the maintenance of feeder-dependent ES cells, under feeder-free conditions in the presence of LIF, is more effective (in inhibiting ES differentiation) when the ES cells are grown on extracellular matrix deposited by fibroblasts rather than on gelatine alone, which is the standard procedure. See also (Abbondanzo et al., *Methods in Enzymology*, 1993)

The feeders can be permanently growing lines (e.g., STO fibroblasts). The advantage of STO cells is that they are continuously proliferating, so they do not need to be repeatedly derived. The disadvantage with STO cells is that there is variation between different sublines, with some being more effective than others at sustaining ES cells. The following procedure, described in Ramirez-Solis et al., *Methods in Enzymology*, 1993, can be used:

1. Coat tissue culture plates with gelatin (Gelatin solution: 1% (w/v) tissue culture grade gelatin mixed in water and sterilized by autoclaving; the working solution is 0.1% and is made by diluting the 1% stock solution in sterile water. Store at room temperature) by covering the bottom of the plate with a 0.1% gelatin solution and incubating at room temperature for 2 hr. Aspirate the gelatin before plating the inactivated feeder cells.

2. Grow $G418^r$ cells to confluence on 15 cm gelatinized tissue culture plates in DMEM plus 7% FCS and 1× GPS. To inactivate the cells, mitomycin C stock solution (0.5 mg/ml) is added to the medium to give a final concentration of 10 ug/ml, and the plate is incubated at 37°, 5% (v/v) $CO_2$, for 2 hr.

3. Aspirate the mitomycin-containing medium and wash the plate twice with PBS.

4. Add 2 ml of trypsin solution and incubate at 37°, 5% $CO_2$, for 5 min.

5. Add 5 ml of medium and suspend the cells by vigorous pipetting. Transfer the cells to a 50-ml sterile centrifuge tube. Wash the plate with medium once again. Pool all the mitomycin-treated cells and centrifuge at 1000 rpm for 5 min at room temperature.

6. Aspirate the supernatant and resuspend the pellet, in 5-10 ml of medium. Count the cells and add medium to give a concentration of $3.5 \times 10^5$ cells/ml.

7. Transfer aliquots of feeders onto gelatinized plates, 12 ml per 10-cm plate ($4.2 \times 10^6$ cells/plate), 4 ml per 6-cm plate ($1.4 \times 10^6$ cells/plate), etc. Leave plates in the incubator overnight before use to give cells time to attach to the plate. Feeder plates can be stored for 3-4 weeks in the incubator, but they should be checked under the microscope before use to confirm that the layer is intact.

E. Isolation of Embryonic Stem Cells from Blastocysts

The following procedure, described in Verstegen, *Journal of Reproduction and Fertility* (1993), can be used:

1. The experimental cats are housed under a lighting schedule of 14 h light and 10 h dark. The cats are fed once daily and allowed access to water ad libitum. Cats are examined daily to ensure that they are not in oestrus or close to the next oestrus period. Allow a 2 week separation between the beginning of the treatment and the end of the previous oestrus period.

2. pFSH without LH activity is reconstituted in physiological saline to a concentration of 2 iu/ml (1 iu=10 ug). Solutions can be aliquoted and stored at −20° C. until use.

3. Inject each cat subcutaneously with 2.0 iu of pFSH daily for five days (each cat receives a total of 10.0 iu of pFSH).

4. On day six inject 1.0 iu of pFSH subcutaneously and 250.0 iu of human chorionic gonadotrophin (hCG) intramuscularly. Repeat these injections on the seventh day.

5. On Days 5, 6, 7, and 8, queens are placed with a fertile male until a minimum of four matings have occurred.

6. The surgical recovery of embryos are performed by uterine lavage between day 11 and day 13 after onset of treatment. The animals are anaesthetized with 100 ug medetomidine/kg and 5 mg ketamine/kg by intramuscular injection.

7. After a midline incision, the ovaries, the uterotubal junction and the body of the uterus are exteriorized.

8. Make a 1.0 mm incision in the uterine body and insert a three-way Swan-Ganz paediatric catheter into one uterine horn. Inflate the cuff to seal the distal end of the horn. At the uterotubal junction, an atraumatic needle is introduced in the uterine lumen and 20 ml of phosphate-buffered saline (PBS) [without Ca and Mg, plus pyruvate-Na (0.36 g/l), kanamycin sulfate (0.25 g/l) and phenol red (0.05 g/l)] warmed to 39° C. is injected twice into the horn. The flushing liquid is recovered via the Swan-Ganz catheter into an aseptic bottle.

9. After recovery, suture the incisions with 5/0 vicryl.

10. Transfer the embryos into a 35-mm culture dish containing PBS with 10% fetal calf serum (PBS-FCS).

The following additional steps, described by Abbondanzo et al., Methods in Enzymology, 1993, are also carried out:

11. Locate the embryos using a stereo dissection microscope with ×20 or ×40 magnification. Once an embryo/blastocyst is identified, it is removed from the dish using a mouth-controlled pipette.

12. Transfer the embryos to a fresh dish of PBS-FCS to wash away any contaminating blood cells or uterine tissue and discard any unfertilized eggs/embryos.

13. The blastocysts are transferred to 60-mm dishes containing pre-pared feeders, adding no more than 20 to each dish. The ES-DMEM medium is supplemented with 1000 IU of recombinant LIF (murine or human is equally effective). The dishes with the embryos are returned to a 370 incubator and left undisturbed for 2 days.

14. Over this period, embryos will hatch from the zona pellucida and attach to the surface of the dish. The trophoblast spreads out to form a monolayer of cells on which the inner cell mass (ICM) can be seen. Over the next 2 days (i.e., up to day 4 from the time of explanting the blastocysts), the ICM grows and forms a distinct mound of cells on the trophoblast monolayer. At the end of 4 days and in the first half of the fifth day of culture, the ICMs should be picked for disaggregation. There appears to be an optimal window in time when the ICM is best suited for producing ES lines. Generally, blastocysts are too far developed if picked any period after 5 days of explanting, and the frequency of forming ES lines declines. This point can often be recognized by the formation of an endoderm layer around the core of ICM. These explants rarely, if ever, give rise to ES lines.

15. To pick the ICMs, the culture medium is aspirated and the dish washed twice in $Ca^{2+}/Mg^{2+}$-free PBS, with embryos remaining covered by the PBS. Microdrops of 0.25% trypsin and 1.0 mM EDTA plus 1% chicken serum are set up under paraffin oil. Chicken serum is included in the trypsin-EDTA solution because, unlike FCS, it does not contain a trypsin inhibitor, and the added protein protects the cells from lysis.

The ICMs are picked off the trophoblast by gently dislodging them using a mouth-controlled pipette. Each ICM is then transferred into a single microdrop of trypsin-EDTA solution plus 1% chicken serum and left for approximately 3-5 min. The cells in the ICM clump start to lose contact with each other. Using another mouth-controlled pipette, whose tip has been flame-polished to remove any sharp edges and whose diameter is between 50 and 100 um, the clumps are broken up into smaller clusters of cells and single cells by pipetting up and down a few times. The entire cell suspension is transferred to a single well of a 16-mm tissue culture dish which already contains a fibroblast feeder layer. The culture medium (1 ml) is ES-DMEM supplemented with 1000 IU of LIF. Use Nunclone 4×16 mm well multidishes (Nunc) as the culture vessel for the disaggregated ICMs, allowing one well per ICM. When all the ICMs have been disaggregated and each one has been transferred to a well, the culture dishes are returned to the incubator.

16. Between 3 and 4 days after explanting the ICMs, the wells should be inspected to check that ICM cells are present and have started to form colonies. The explanted ICM cells do not just give rise to ES cells. In many instances, other cell types appear with the continued culture of the primary explants. These colonies may at first resemble ES colonies. However, over time they differentiate and cease to proliferate. ES cell colonies, which have a characteristic morphology continue to proliferate, usually as tight round colonies that have smooth edges. It is difficult to distinguish the individual cells in the colony, although their nuclei can be recognized and contain one or two prominent nucleoli. By observing the well on a daily basis, it is possible to see whether a colony continues to increase in size as it proliferates without differentiation. These colonies are most often found at the perimeter of the well, which is sometimes difficult to view with a tissue culture microscope. Careful inspection should therefore be made of the perimeter to ensure that no colonies are missed. ES colonies should be apparent within 7-10 days after picking and disaggregating the ICM.

It appears that using early passage (P2-3) fibroblasts and including recombinant LIF in the culture medium can help in the establishment of ES cells from the disaggregated ICMs. Overall, ES lines can be established at a frequency of 10-30% from the picked ICMs.

F. Expansion of Embryonic Stem Cells

When colonies of ES cells have been identified in the primary explants, their numbers can be expanded. It is not necessary to isolate the ES cells in the primary cultures from other differentiated cell types that may be present, since one of the characteristics of ES cells is rapid and continuous proliferation.

The entire well containing the ES colonies is washed 2 times in PBS, and the PBS is aspirated. To each well, 0.2 ml of trypsin solution plus 1% chick serum is added, and the well is left to trypsinize for 5 min. Then 0.5 ml of ES-DMEM is added, and all clumps of cells are broken up by gently pipetting the suspension, with care being taken to ensure that no bubbles are introduced into the well. If only one or two ES colonies are present in the well, the cell suspension is left in the well to reattach. The medium is replaced, the next day, with 1 ml of ES-DMEM plus 1000 IU/ml LIF. Over the next 3-5 days, if ES colonies were correctly identified, many new colonies of ES cells should become visible. The well can then be trypsinized again and the contents transferred to a 60-mm dish containing a fibroblast feeder layer. The colonies of ES cells should continue to proliferate without differentiation. At this point, it is no longer necessary to include LIF and the cells can be maintained on feeder layers in ES-DMEM. See procedure described in Abbondanzo, supra.

G. Expansion, Freezing, and Routine Culture of Embryonic Stem Cells

Once an ES line has been found to contain a high percentage of cells with a normal diploid karyotype, it should be expanded so that as many early passage cells as possible are frozen in liquid nitrogen. This will provide sufficient resources for future experiments, since early passage ES cells tend to make better chimeras at a higher frequency than if passages 15-20 and later are used. However, there is no absolute correlation, since relatively late passage lines such as D3 have been reported to produce germ line chimeras.

The ES cells can be maintained as an undifferentiated population by trypsinizing and replating the cells onto dishes containing fresh feeders, every 5-6 days if the cells are plated out at a sufficiently low density. A 60-mm dish at maximum density will contain about $1-2 \times 10^7$ ES cells, and a 150-mm dish can contain up to $2-3 \times 10^8$ cells at maximal density. The cells will start to differentiate or die if they are maintained beyond the maximum density level, and thus the optimal period of time they can be maintained before they have to be passaged is about 5-7 days. To maintain a line, trypsinizing a semiconfluent dish and plating out of the single cell suspension with 1:100 to 1:500 dilution is sufficient. If the cells are replated at reasonably low density, the culture medium needs changing every other day to keep cells under optimal conditions. If more cells and higher densities are required, then the cells should be refed every day. Under optimal conditions, the ES cells should grow as small clusters or mounds. If the conditions are suboptimal, differentiated derivatives will appear, and the mounds of ES cells will start to flatten out, with individual cells becoming more distinct. Under extreme conditions the majority of the cells will have differentiated. For a general description of this technique, see Abbondanzo, supra.

H. Freezing of Embryonic Stem Cells

The following technique, described by Abbondanzo, supra, can be used.

1. A culture of ES cells should be in the log phase of growth, that is, not at maximal density. Wash the dish 2 times in PBS and trypsinize.

2. Harvest the cells, resuspended in medium, and count with a hemocytometer.

3. The medium for freezing the cells consists of a 50:50 mixture of DMEM and FCS containing a final concentration of 10% (v/v) dimethyl sulfoxide (DMSO) (Sigma).

4. One milliliter of medium containing $1-5 \times 10^6$ ES cells is aliquoted into a 1-ml sterile freezing vial (Nunc) that has a screw cap and rubber seal.

5. The vials are labeled with the ES line and passage number, placed in a holding rack, and left overnight in a $-70°$ freezer.

6. The following day the frozen vials should be transferred to a liquid nitrogen container for long-term storage.

7. To thaw ES cells, a 60-mm tissue culture dish containing a feeder layer in ES-DMEM medium should be prepared in advance. Remove the vial of ES cells and place in a beaker of sterile distilled water prewarmed to 37° until the contents of the vial have melted. Remove the vial, swab with 100% ethanol to sterilize the outside, and remove the cell suspension with a sterile Pasteur pipette. The cells can be immediately plated out in the 60-mm dish. The next day the culture medium is replaced with fresh ES-DMEM to remove all the DMSO and any dead cells. If freezing and thawing of the ES cells were performed correctly, then ES colonies should already be visible in the culture dish.

III. Gene Targeting

Gene targeting, or site-directed recombination, are standard laboratory techniques that makes use of a natural cellular mechanism known homologous recombination for interchanging DNA sequences and thereby replace or disrupt all or part of an endogenous genomic sequence with another desirable polynucleotide. Gene targeting can therefore be used to knock out, delete, or prevent normal expression of an entire gene or its exons or to introduce point mutations, for example.

Under the natural cellular mechanism, any pair of DNA sequences that share sequence identity, i.e., they are "homologous" sequences, can interact to form a new recombinant DNA species. The success rate of such desired homologous recombination events, however, increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

A polynucleotide of interest, therefore, can be linked in a vector to sequences that share homology with endogenous sequences of the host cell. Those sequences are referenced herein as "homology arms." Eventually, the homologous sequences (the ones in the vector and their genomic counterparts) interact or "recombine" to insert the desired polynucleotide to which they are linked in the vector at the site where the homologous genomic DNA sequences were located. Therefore, the choice of sequences for the homology arms will determine the site at which the desired polynucleotide is integrated into the genome.

If the desired polynucleotide insert is linked to homology arms that share homology to a single copy gene, then it, the desired polynucleotide, will be inserted via homologous recombination at only that single specific site. If, on the other hand, the desired polynucleotide is linked to homology arms that share homology to a multi-copy gene, then the desired polynucleotide can be inserted via homologous recombination at each of the specific sites where a copy of the gene is located.

A desired DNA sequence can be inserted into a genome by a homologous recombination reaction that involves either (1) a single reciprocal recombination, which results in the insertion of the entire length of the introduced DNA, or (2) a double reciprocal recombination, which results in the insertion of only the DNA located between the two recombination events.

To insert a foreign gene into the genomic site, for example, Fel d I, the introduced vector should contain sequences homologous to the genomic Fel d I gene. A single homologous recombination event would result in the entire introduced DNA sequence being inserted into the genomic Fel d I gene locus. Alternatively, a double recombination event can be achieved by flanking each end of the desired polynucleotide that is destined to be inserted into the genome with homology arms that are homologous to sequences of the Fel d I gene. One or both of the homology arms may also comprise sequences outside of the Fel d I gene or locus, such as adjacent flanking sequences that are upstream or downstream of the 5'-end or 3-end of the particular Fel d I sequence of interest. A homologous recombination event involving each of those two homology arms that flank the desired polynucleotide will result in the insertion of the desired polynucleotide into the genome.

Against this background, and according to the present invention, any part of the Fel d I gene locus may be so disrupted. That is, gene targeting techniques can be used to (A) knock out or delete the entire Fel d I locus, which includes the Fel d I gene sequence that encode "chain 1" and "chain 2" (see B. below); (B) knock out either all or a part of the gene encoding chain 1 or all or a part of the gene encoding chain 2; (3) knock out all of one chain and a part of the other chain; (4) knock out one or more specific exons from either of the Fel d I chain sequences; (5) knock out all or part of the Fel d I promoter sequence; (6) substitute, i.e., replace, one or more nucleotides or a stretch of contiguous nucleotides present in the Fel d I locus, with another different nucleotide, other different nucleotides, or another stretch of contiguous nucleotides that is not 100% identical in sequence to the target sequence; or (7) insert a desired polynucleotide into the genomic sequence. The present invention is not limited to these exemplary gene targeting events.

Hence, the present invention contemplates knocking out, deleting, replacing, substituting, or otherwise disrupting at least some part of the Fel d I gene sequences, which includes the exons and introns that encode the Fel d I gene sequence for chain 1, the exons and introns that encode the Fel d I gene sequence for chain 2, and the sequence of the Fel d I gene promoter. The present invention also contemplates inserting a desired sequence into the genome. Any of these methods may disrupt the normal expression of the endogenous genomic Fel d I sequence to such extent that there is no, or only a partial, Fel d I RNA transcript produced, such that little, if any, Fel d I protein is produced. This could be because either one or both chains 1 and 2 are not expressed, or because the disruption caused a Fel d I mutant protein to be expressed. Thus, it is desirable under the present invention that expression of any Fel d I gene sequences after the animal genome has been targeted according to the present invention, produces little, if any, of the native Fel d I protein allergen.

In this context, it is possible to target and disrupt any exon of the Fel d I gene so long as the effect of that disruption is to reduce or prevent expression of a functional and normal Fel d I protein. It is possible that by only targeting the disruption of one or a few exons that a mutant Fel d I protein could be made that still comprises allergenic epitopes. In the Fel d I system, however, disrupting the first exon can be very desirable because the start codon for the gene is present within that exon, which dictates the reading frame for transcription and translation purposes. Hence, disrupting that particular exon to remove the start codon could very well prevent expression of the gene sequence entirely. It can be desirable to remove essentially all of the coding sequences of both chains, chains 1 and 2, of Fel d I and all of the sequences for the Fel d I promoter, too.

Figure 7:
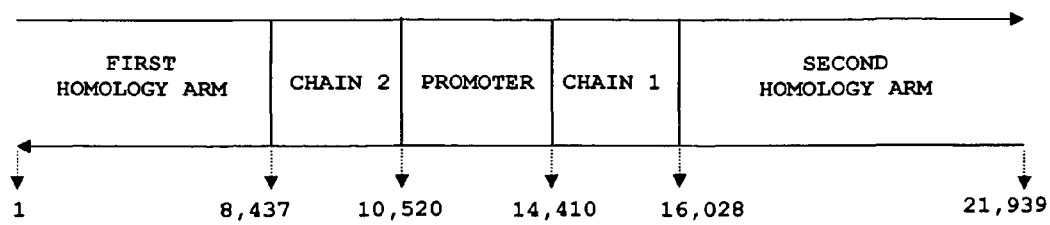
FIG. 7. depicts a schematic of the Fel d I gene locus in which is shown chains 1 and 2 and the Fel d I promoter, as well as the sequence regions that can be used to design sequences appropriate for the recombination vector homology arms.

A nucleotide sequence of about 21,939 bp in length for Fel d I was identified by the present inventions and is depicted in SEQ ID NO. 7 (FIG. 7). It comprises DNA sequences identified by the present inventors that are useful for performing any of these homologous recombination events. As depicted in FIG. 7, the top strand is the positive strand, while the bottom-most strand is the negative strand of the DNA duplex representing the genomic Fel d I sequence. The coding sequence, which includes exons and introns for the Fel d I chain 1 runs from the nucleotide positioned at about 14,410 of SEQ ID NO. 7 to about nucleotide 16,028 of the positive strand. The coding sequence, which includes exons and introns for the Fel d I chain 2 runs from about nucleotide position 10,520 to about 8,437 on the negative strand. There are approximately 3,888 nucleotides separating the respective start codons of chains 1 and 2. The Fel d I promoter is positioned approximately in the region 10,521-14,409. This sole promoter drives expression of both chains 1 and 2. See FIG. 7 for a schematic representation of the organization of the Fel d I genomic locus.

If it is desirable to perform homologous recombination on the entire Fel d I gene, i.e., to knock out both chains 1 and 2 and the promoter, then homology arms can be created from any portion of SEQ ID NO. 7 that flanks the denoted end points of the chains. Hence, according to the present invention, homology arms can be created from any sequence stretching from nucleotide 1 to about nucleotide 8,437 of SEQ ID NO. 7, which abuts the sequence for chain 2, or from about 16,029 to nucleotide 21,939, the end of the SEQ ID NO. 7 sequence. Thus, a first homology arm for this purpose may comprise any length of sequence from 1-8437. A second homology arm for this purpose may comprise any length of sequence from 16029-21939. Of course, it is not critical, in any embodiment of the present invention, that the sequence of any particular homology arm excludes a particular chain DNA sequence. That is, in this particular embodiment, where both chains 1 and 2 and the promoter are to be knocked out, it is not fatal to recombination or the invention if the sequence of one or both of the homology arms extends into chain 1 or chain 2, respectively. For instance, the first homology arm might stretch from nucleotide 7,000 to nucleotide 9,000, and therefore into the 3'-end of the chain 2 encoding sequence, and still be functionally useful for homologous recombination purposes. Indeed, the present invention explicitly contemplates such sequence designs.

A homologous recombination construct of the present invention for knocking out chain 1, chain 2, and the promoter may therefore comprise (1) a first homology arm that comprises, for instance, nucleotides 5,000-8,000 of SEQ ID NO. 7; (2) a second homology arm that comprises, for instance, nucleotides 15,000-18,000; and (3) a desired polynucleotide that is positioned in between the first and second homology arms.

By similar approaches, homology arms can be designed that flank any portion that is desired to be targeted in the endogenous genome. Thus, to disrupt chain 1 only, one may design a first homology arm that comprises the sequence between nucleotides 5,000-8,000 of SEQ ID NO. 7, and a second homology arm that comprises the sequence between nucleotides 11,000-13,000 of SEQ ID NO. 7, for instance. The desired polynucleotide destined for integration into the native genome would be positioned, again, between those two homology arms. Upon recombination, the desired polynucleotide will replace the chain 1 sequence. Likewise, to disrupt chain 2, one could design a first homology arm that extends from nucleotide 12,000 to nucleotide 14,000 of SEQ ID NO. 7, and a second arm from nucleotide 17,000 to 19,000 of SEQ ID NO. 7. Similarly, to disrupt the Fel d I promoter, one could design a first homology arm that comprises the sequence from 8,000-10,000 of SEQ ID NO. 7, and a second homology arm from 15,000 to 17,000 of SEQ ID NO. 7. Of course, these examples are merely exemplary of potential homology arms that can be designed to target one or more regions of the Fel d I gene sequences depicted in SEQ ID NO. 7.

A homology arm may be of any length, such as less than about 1,000 nucleotides in length, or about 1,100 nucleotides in length, about 1,200 nucleotides in length, about 1,300 nucleotides in length, about 1,400 nucleotides in length, about 1,500 nucleotides in length, about 1,600 nucleotides in length, about 1,700 nucleotides in length, about 1,800 nucleotides in length, about 1,900 nucleotides in length, about 2,000 nucleotides in length, about 2,100 nucleotides in length, about 2,200 nucleotides in length, about 2,300 nucleotides in length, about 2,400 nucleotides in length, about 2,500 nucleotides in length, about 2,600 nucleotides in length, about 2,700 nucleotides in length, about 2,800 nucleotides in length, about 2,900 nucleotides in length, about 3,000 nucleotides in length, about 3,100 nucleotides in length, about 3,200 nucleotides in length, about 3,300 nucleotides in length, about 3,400 nucleotides in length, about 3,500 nucleotides in length, about 3,600 nucleotides in length, about 3,700 nucleotides in length, about 3,800 nucleotides in length, about 3,900 nucleotides in length, about 4,000 nucleotides in length, about 4,100 nucleotides in length, about 4,200 nucleotides in length, about 4,300 nucleotides in length, about 4,400 nucleotides in length, about 4,500 nucleotides in length, about 4,600 nucleotides in length, about 4,700 nucleotides in length, about 4,800 nucleotides in length, about 4,900 nucleotides in length, about 5,000 nucleotides in length, about 5,100 nucleotides in length, about 5,200 nucleotides in length, about 5,300 nucleotides in length, about 5,400 nucleotides in length, about 5,500 nucleotides in length, about 5,600 nucleotides in length, about 5,700 nucleotides in length, about 5,800 nucleotides in length, about 5,900 nucleotides in length, about 6,000 nucleotides in length, about 6,100 nucleotides in length, about 6,200 nucleotides in length, about 6,300 nucleotides in length, about 6,400 nucleotides in length, about 6,500 nucleotides in length, about 6,600 nucleotides in length, about 6,700 nucleotides in length, about 6,800 nucleotides in length, about 6,900 nucleotides in length, about 7,000 nucleotides in length, about 7,100 nucleotides in length, about 7,200 nucleotides in length, about 7,300 nucleotides in length, about 7,400 nucleotides in length, about 7,500 nucleotides in length, about 7,600 nucleotides in length, about 7,700 nucleotides in length, about 7,800 nucleotides in length, about 7,900 nucleotides in length, about 8,000 nucleotides in length, about 8,100 nucleotides in length, about 8,200 nucleotides in length, about 8,300 nucleotides in length, about 8,400 nucleotides in length, about 8,500 nucleotides in length, about 8,600 nucleotides in length, about 8,700 nucleotides in length, about 8,800 nucleotides in length, about 8,900 nucleotides in length, about 9,000 nucleotides in length, about 9,100 nucleotides in length, about 9,200 nucleotides in length, about 9,300 nucleotides in length, about 9,400 nucleotides in length, about 9,500 nucleotides in length, about 9,600 nucleotides in length, about 9,700 nucleotides in length, about 9,800 nucleotides in length, about 9,900 nucleotides in length, about 10,000 nucleotides in length, about 10,100 nucleotides in length, about 10,200 nucleotides in length, about 10,300 nucleotides in length, about 10,400 nucleotides in length, about 10,500 nucleotides in length, about 10,600 nucleotides in length, about 10,700 nucleotides in length, about 10,800 nucleotides in length, about 10,900 nucleotides in length, about 11,000 nucleotides in length, about 12,000 nucleotides in length, about 13,000 nucleotides in length, about 14,000 nucleotides in length, about 15,000 nucleotides in length, about 16,000 nucleotides in length, about 17,000 nucleotides in length, about 18,000 nucleotides in length, about 19,000 nucleotides in length, about 20,000 nucleotides in length, about 21,000 nucleotides in length, or about 22,000 nucleotides in length, or more than about 22,000 nucleotides in length.

The first and second homology arms do not have to be the same length as each other. Furthermore, a homology arm does not, according to the present invention, have to be 100% identical in sequence across its entire length to the corresponding sequence of the Fel d I gene with which it will recombine. Thus, a homology arm may share a percentage of sequence identity with an endogenous sequence, which is about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, 90%, about 91%, about 92%, about 93%, about 94%, about 795%, about 96%, about 97%, about 98%, or about 99% identical with the endogenous sequence with which it is to recombine and still perform functionally to facilitate homologous recombination.

A homology arm, as seen above, can be quite long. According to the present invention, therefore, a homology arm may comprise 100% sequence identity to an endogenous sequence over only a portion of its length, whilst other portions of the homology arm share less than 100% sequence identity with the endogenous sequence, but such an arm is still functional for homologous recombination purposes. Hence, the present invention contemplates a homology arm that contains regions of high and low sequence identity to the endogenous sequence, but is still functional to perform homologous recombination.

As used herein, "sequence identity" or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237-244 (1988); Higgins and Sharp, *CABIOS* 5: 151-153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995); Altschul et al., *J. Mol. Biol.*, 215:403-410 (1990); and, Altschul et al., *Nucleic Acids Res.* 25:3389-3402 (1997).

Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l Acad. Sci. USA* 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Clayerie and States, *Comput. Chem.*, 17:191-201 (1993)) low-complexity filters can be employed alone or in combination.

Multiple alignment of the sequences can be performed using the CLUSTAL method of alignment (Higgins and Sharp (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

A gene targeting homologous recombination vector can therefore be created using the principles and rationales set forth herein to link together DNA sequences that perform the desired targeted genomic disruption. Such a homologous recombination vector construct is discussed in more detail below but it may comprise (1) the polynucleotide sequence of interest, which is flanked by (2) a first homology arm, and (3) a second homology arm, as described herein. As described above, a homology arm of the present invention, may, for instance, be designed in accordance with the rationales set forth in the preceding passages, to comprise any sequence of SEQ ID NO. 7, and be of any length, such as those lengths described above. Furthermore, the present invention is not limited to targeting of only genomic sequences. For ease of describing the invention, the term "genomic" and "endogenous" are used, but the concepts for targeting a DNA sequence in these environments are contemplated in this invention, such as targeting of other DNA sources, such as mitochondrial DNA, extrachromosal DNA, DNA from another vector, or DNA that has infected a particular cell, such as viral, fungal, or bacterial DNA.

As used herein a "part" or "fragment" of a desired polynucleotide, gene, or of the Fel d I gene, may include any stretch of contiguous nucleotides. Thus a nucleic acid or polynucleotide that contains a "part" of the Fel d I gene, for instance, may include about 10 contiguous nucleotides, about 15 contiguous nucleotides, about 20 contiguous nucleotides, about 25 contiguous nucleotides, about 30 contiguous nucleotides, about 35 contiguous nucleotides, about 40 contiguous nucleotides, about 45 contiguous nucleotides, 50 contiguous nucleotides, about 55 contiguous nucleotides, about 60 contiguous nucleotides, about 65 contiguous nucleotides, about 70 contiguous nucleotides, about 75 contiguous nucleotides, about 80 contiguous nucleotides, about 85 contiguous nucleotides, 90 contiguous nucleotides, about 95 contiguous nucleotides, about 100 contiguous nucleotides, about 110 contiguous nucleotides, about 115 contiguous nucleotides, about 120 contiguous nucleotides, about 125 contiguous nucleotides, about 130 contiguous nucleotides, about 135 contiguous nucleotides, about 140 contiguous nucleotides, about 145 contiguous nucleotides, about 150 contiguous nucleotides, about 200 contiguous nucleotides, about 300 contiguous nucleotides, about 400 contiguous nucleotides, about 500 contiguous nucleotides, about 600 contiguous nucleotides, about 700 contiguous nucleotides, about 800 contiguous nucleotides, about 900 contiguous nucleotides, about 1,000 contiguous nucleotides, about 2,000 contiguous nucleotides, about 3,000 contiguous nucleotides, about 4,000 contiguous nucleotides, about 5,000 contiguous nucleotides, about 6,000 contiguous nucleotides, about 7,000 contiguous nucleotides, about 8,000 contiguous nucleotides, about 9,000 contiguous nucleotides, or about 10,000 contiguous nucleotides, or more than about 10,000 contiguous nucleotides, including any number of contiguous nucleotides that fall within any range of nucleotides described herein, i.e., a "part" of a Fel d I gene could include, but is not limited to a length that is somewhere between about 100-1,000 nucleotides, between about 1,000-5,000, nucleotides, or between about 5,000-10,000 or more nucleotides.

The desired polynucleotide that is linked to the homology arms may be any DNA sequence, such as a different gene, or a positive or negative selectable marker, or the desired polynucleotide may be a mutated version of an endogenous sequence. In the context of the Fel d I gene, for instance, the desired polynucleotide might be essentially identical to a portion of the native chain 1-encoding DNA sequence, but comprises one or more point mutations, deletions or insertions, whereupon homologous recombination using homology arms designed to Fel d I sequences that flank that particular target site, will effectively cause substitution of that native chain 1 DNA sequence for the mutated version as engineered into the desired polynucleotide. The following additional embodiments elaborate on this general scheme for knocking out some or all of the Fel d I gene sequences.

A. Culture of Embryonic Stem Cells

The following procedure is adapted from the protocol described in Ramirez-Solis, Davis, and Bradley, "Gene Targeting in Embryonic Stem Cells." *Methods in Enzymology*, (1993).

The purpose of using ES cells for gene targeting is to transfer the mutation generated in culture into the cat germ line. For this reason, culture conditions that prevent the overgrowth of abnormal cells are critical. ES cells should be grown on mitotically inactivated feeder cell layers. In addition, the cells should be grown at high density and passaged frequently at 1:3 to 1:6; this usually means replacing the medium daily. ES cells should be fed 4 hr before passage. To passage, the cells should be washed twice with PBS and trypsinized for 10 min; there is no need to prewarm the trypsin solution. ES-DMEM medium is added, and the cell clumps are mechanically disrupted by vigorous pipetting. It is important to generate a single cell suspension before passage as clumps have a tendency to differentiate. The passage number of the cell line should be recorded to give an estimate of the time the cells have been in culture. If the cells are not to be used immediately, they should be frozen and then recovered when needed.

The cultured ES cell population includes totipotent cells, as well as cells with limited potential to contribute to all tissues of the cat. Be-cause targeted events are usually rare and single cell cloning is necessary, it is advisable to optimize targeting vectors and conditions such that several targeted clones can be recovered. Also, cloning involves culture at low cell concentrations and potentially for a prolonged period while screening for the desired clone.

B. Genes Encoding Fel d I

Two genes encode for the protein chains that comprise the major cat allergen, Fel d I. The protein chains are designated as "chain 1" (or Ch 1) and "chain 2" (or Ch 2). One published polynucleotide sequence for the Fel d I gene is described in Griffith, et al. Expression and Genomic Structure of the Genes Encoding FdI, the Major Allergen from the Domestic Cat, *Gene,* 113(2): 263-8 (1992), which is shown in FIGS. 2 and 3. See also Morgenstern, et al., *Proc. Nat'l. Acad. Sci. USA,* 88:9690 (1991).

Ch 1 is composed of a mature protein subunit of 70 aa. Sequencing of the gene encoding for Ch 1 demonstrates that there are two alternative Ch 1 leader sequences with the leader B exon separated from the start of the leader A exon by an intron of 46 bp. The junction of leader B (exon 1) or leader A (exon 2) with exon 3 leads to alternative codons that encode either Asp (leader B) or Asn (leader A). These junctions (exon 1/3 and exon 2/3) are positioned 2 aa from the N terminus of the mature Ch 1, which starts with $Glu^1$. The structural gene is comprised of only two exons, 3 and 4, that encode the mature protein (FIG. 2).

Ch 2 is composed of a mature protein subunit of 92 aa. The leader sequence and the first 3 aa of the mature protein are encoded by exon 1 (61 nt; 20 aa). The bulk of the mature protein is encoded by exons 2 and 3 (aa 4-64 and 65-90, respectively). The first 18 nt of exon 3 encode the residues, IAINEY (aa 65-70), rather than the published sequence, TTISSSKD, suggesting that Ch2 has two forms (FIG. 3).

While any of the exons can be targeted by the vector construct, it is preferential to allow for at least 1000 bp of homology on either side of the targeted exon. It has been demonstrated that this contributes to a greater success rate of recombination events.

C. Vector Design

1. General Vector Design with Selectable Mutations

Generally, gene targeting by homologous recombination occurs at a low frequency in comparison to random integration events. For most genes, vectors as described in the preceding passages, can be designed to reduce the frequency of random integration events surviving selection. A gene that is expressed in ES cells can be targeted using a selectable marker with no promoter. The selectable marker can either have its own translation initiation signal or form a fusion protein with the targeted gene. Alternatively, the selectable marker can be placed within the gene so that the polyadenylation signal must be supplied by the genomic integration site.

For any gene, a negative selectable marker (i.e., $strp^s$) can be used outside the homologous region in the targeting vector. In a correct targeting event, the negative selectable marker will be excised and the cells will be resistant to streptomycin, but in the random events, the negative marker will generally be integrated and expressed, causing cell death via metabolism of the toxic nucleoside analog. These strategies can be used alone or in combination to help increase the relative gene targeting frequency. The number of clones with random integration events that survive selection will be reduced which will make the targeted event easier to detect.

The factors that determine the frequency with which a genomic locus will be targeted have not as yet been determined completely. Factors which do affect the targeting frequency include the length of perfect homology between the targeting vector and the genomic locus, the placement of the selectable marker within the homologous stretch, and the site of linearization of the vector. The standard replacement vector using positive-negative selection has shown targeting frequencies of 1/10 to 1/1000 $G418^r$-$strp^s$ colonies for many genes. Regarding the length of homologous sequences in the targeting vector, a convenient compromise between vector construction, diagnosis of targeted events, and targeting frequency may be about, for instance, about 3 kb with at least about 1 kb on either side of the selectable marker, but the present invention is not limited to this particular embodiment, as explained above.

In this respect, the present invention contemplates the use of any sequences from SEQ ID NO. 7 for constructing such a homologous recombination vector. SEQ ID NO. 7 is 22,250 nucleotide long genomic Fel d 1 DNA sequence that is useful in this regard. The Fel d 1 chain 1 coding sequence, including introns and exons, is located between nucleotides 14,720 to 16,338, on the positive strand (top) of SEQ ID NO. 7. The Fel d 1 chain 2 coding sequence, including introns and exons, is located between nucleotides 10,830 to 8,747 of the negative strand (bottom) of SEQ ID NO. 7. The Fel d 1 promoter is located between nucleotides 10,831-14,719.

Any contiguous nucleotide stretches of SEQ ID NO. 7 may be used for constructing a homologous recombination vector that can then be used to target the endogenous Fel d 1 gene in the cat genome or the endogenous RNA transcript for Fel d 1 and thereby reduce, disrupt, or abolish expression of Fel d 1 and the resultant protein. Thus, SEQ ID NO. 7 provides useful sequences to create homology "arms" that can be engineered to flank a desired Fel d 1 nucleotide target site. Hence, the present invention contemplates targeting of endogenous Fel d 1 by a vector that has two homology arms oriented to flank a target locus. The length of a homology arm can be any length as described above.

It is desirable to construct the targeting vector with DNA from the same cat strain as the ES cell line since polymorphisms could disrupt the length of perfect homology and result in a lower targeting frequency. Careful consideration should be given to the structure of the locus after the desired recombination event, especially if a null allele is desired. For small genes, replacement vectors can be designed in which the coding sequence is replaced by the selectable marker. For larger genes, disruption of the first coding exon is most likely to give a null allele.

A Fel d I gene can also be disrupted, and inactivation, by deletion of all or part of the Fel d I gene, so as to prevent production of a functional Fel d I protein.

500 colonies are routinely screened by "mini-Southern" analysis (Section F) after the first round of targeting. If targeted clones are found, they should be examined by several digests on Southern analysis using probes and enzymes specific for both the 5' and the 3' ends of the homologous sequences, to ensure that the desired recombination event has occurred. If clones are not identified, it is best to redesign the vector rather than continue further screening.

Insertion vectors have been shown to target between 5- and 12-fold more frequently than replacement vectors and could be used for subsequent attempts at targeting. Depending on the design of the original replacement vector, it may be possible to linearize the same vector within the area of homology to take advantage of the higher targeting frequency of insertion events. For a general discussion of vector design, see Ramirez-Solis et al., *Methods in Enzymology*, 1993.

2. Fel d I Vector Design

Fel d I has the advantage of having two genes that code for the major allergen. This means that constructs can be designed to disrupt the coding sequence of either chain 1 (Ch 1), chain (Ch 2), or both chains. For a general discussion of site directed mutagenesis of target genes, see Thomas and Capecchi, "Site-Directed Mutagenesis by Gene Targeting in Mouse Embryo-Derived Stem Cells" *Cell* (1987).

A specialized construct of the neomycin resistance ($neo^r$) gene is introduced into one of the exons of a cloned fragment of either Ch 1 or Ch2. This construct is then used to transfect the ES Cells. The $neo^r$ gene is used both to disrupt the coding sequence of the target gene and as a tag to monitor the integration of the newly introduced DNA into the recipient genome. Effective use of the $neo^r$ gene as a tag requires expression of the gene at the appropriate Fel d I locus.

Figure 6:
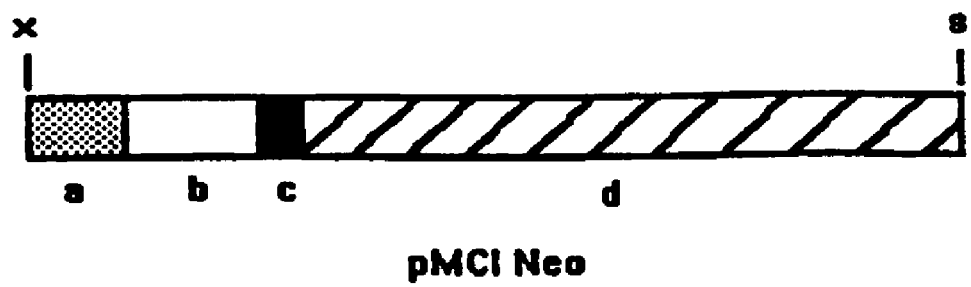
FIG. 6. depicts the construction of the neo$^r$ gene. The structural gene and its control elements are contained on a 1 kb cassette flanked by an XhoI site (x) and a SalI site (s) in a pUC derivative plasmid. (a) A tandem repeat of the enhancer region from the polyoma mutant PYF441 consisting of bases 5210-5274. (b) The promoter of HSV-tk, from bases 92-218. (c) A synthetic translation initiation sequence, GCCAAT ATGGGATCGGCC. (d) The neo$^r$ structural gene from Tn5, including bases 1555-2347.

The neomycin gene is designed to optimize expression in ES cells while maintaining its size at a minimum. The $neo^r$ has been modified for this purpose and is designated pMC1Neo, and the overall structure for this construct is shown in FIG. 6. The neomycin protein coding sequence (d) is from the bacterial transposon Tn5, including bases 1555-2347. The promoter (b) that drives the $neo^r$ gene is derived from the herpes simplex virus thymidine kinase gene (HSV-tk) from bases 92-218. This promoter appears to be effective in embryonal carcinoma (EC) cells. To increase the efficiency of the tk promoter, a duplication of a synthetic 65 bp fragment (a) consisting of bases 5210-5247 of the PyF441 polyoma virus enhancer is introduced. This fragment encompasses the DNA sequence change that allows the polyoma mutant to productively infect EC cells. Finally, because the native $neo^r$ gene translation initiation signal is particularly unfavorable for mammalian translation, a synthetic translation initiation sequence (c) (GCCAATATGGGATCGGCC) is substituted using Kozak's rules as a guide (Kozak, 1986) (FIG. 6). See Thomas and Capecchi, supra for a discussion of this construct.

There are two schemes to disrupt the Fel d I genes: one by sequence replacement vectors and one by sequence insertion vectors. Both vectors contain an exon interrupted with the $neo^r$ gene.

Sequence replacement vectors are designed such that upon linearization, the vector sequences remain collinear with the endogenous sequences. Following homologous pairing between vector and genomic sequences, a recombination event replaces the genomic sequences with the vector sequences containing the $neo^r$ gene (FIG. 4).

Figure 5:
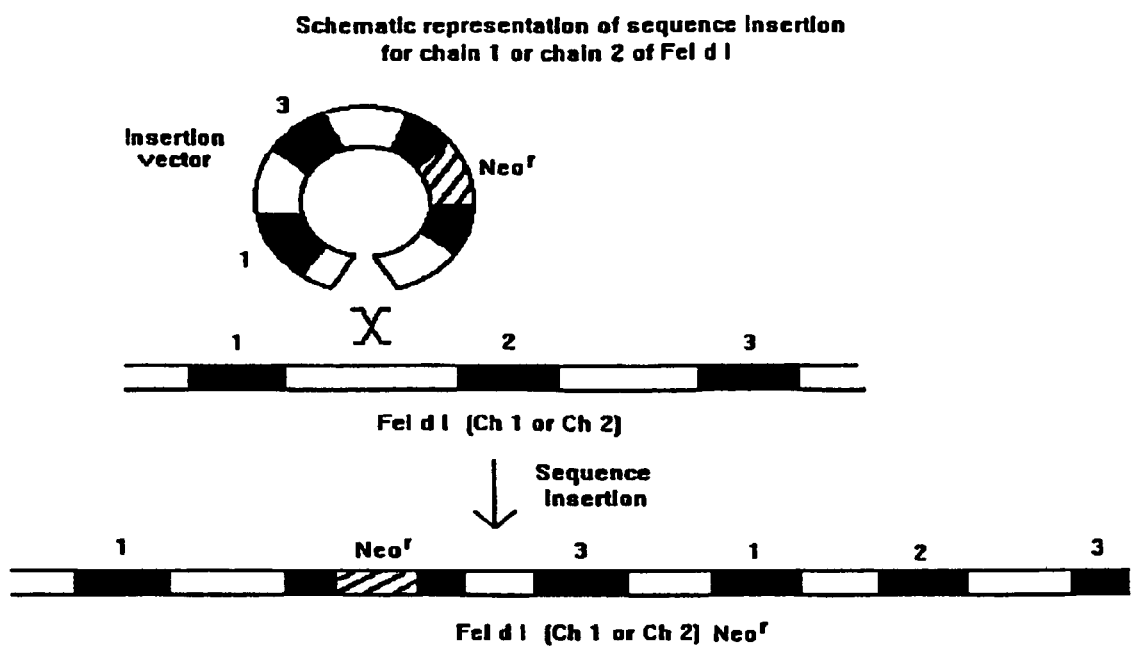
FIG. 5. depicts a schematic for a sequence insertion vector. Sequence insertion vectors are designed such that the ends of the linearized vector lie adjacent to one another on the Fel d I map. Pairing of these vectors with their genomic homolog, followed by recombination at the double strand break, results in the entire vector being inserted into the endogenous gene. This produces a duplication of a portion of the Fel d I gene. Open boxes indicate introns; closed boxes indicate exons; the crosshatched box indicates the neo$^r$ gene.

Sequence insertion vectors are designed such that the ends of the linearized vector lie adjacent to one another on the gene map. Pairing of these vectors with their genomic homolog, followed by recombination at the double strand break, results in the entire vector being inserted into the endogenous gene (FIG. 5).

Successful homologous recombination after electroporation renders the ES cells resistant to the drug G418r. To make initial screening easier, a streptomycin sensitive gene can be added outside of the homologous coding region of the replacement vector. Upon successful gene replacement, this $strp^s$ gene is lost and ES cell colonies will grow on media containing streptomycin. If the recombination is random in the genomic DNA, the $strp^s$ gene will be retained and the ES cells will not grow.

D. Electroporation

The first step of any targeting experiment is the introduction of DNA into the recipient cells. For ES cells, DNA microinjection and electroporation have been shown to be useful to permit gene targeting. DNA microinjection is technically difficult and has the potential to cause gross chromosomal disruption, which may lower the potential of the ES cells to populate the germ line of chimeras. Electroporation, on the other hand, has been used extensively to generate targeted clones that have gone through the germ line. The electroporation protocol used is basically similar to those used for other cell types, but some things are particularly important for the specific case of electroporation of ES cells. The cells should be growing actively at the time of the electroporation; this can be achieved by passaging the ES cells 1 day before the electroporation and adding fresh medium a few hours before harvesting the cells. The trypsin treatment should be long enough to allow mechanical disaggregation of the cell clumps to avoid differentiation. The electroporated cells should be plated on feeder cells with M15 medium within 5-10 min. The following procedure, described in Ramirez-Solis et al., Methods in Enzymology, 1993, can be used:

1. Prepare targeting vector DNA by the CsCl banding technique.
2. Cut 200 ug of targeting vector DNA with the appropriate restriction enzyme to linearize it. Assess the completion of the restriction digest by agarose gel electrophoresis.
3. Clean the DNA with phenol-chloroform, chloroform, and precipitate it with NaCl and ethanol. Resuspend the DNA in sterile 0.1× Tris-EDTA buffer (TE) and adjust the concentration to 1 mg/ml.
4. One day before the electroporation, passage the actively growing ES cells (~80% confluent) 1:2.
5. Feed the cells with fresh M15 medium 4 hr before harvesting them for the electroporation.
6. Wash the plates twice with PBS and detach the cells by treatment with trypsin solution for 10 min at 37° (1 ml trypsin solution for a 10-cm plate).
7. Stop the action of the trypsin solution by adding 1 volume of M15 medium and dissociate the cell clumps by moving the cell suspension up and down with the transfer pipette.
8. Centrifuge the cells at 1000 rpm for 5 min in a clinical centrifuge and discard the supernatant. Resuspend the cells in 10 ml of PBS and determine the total number of cells.
9. Recentrifuge the cells, aspirate the supernatant, and resuspend the cells in PBS at a final density of $1.1 \times 10^7$ cells/ml.
10. Mix 25 ug of the linearized targeting vector with 0.9 ml of the cell suspension in an electroporation cuvette. Incubate for 5 min at room temperature.
11. Electroporate in the Bio-Rad Gene Pulser at 230 V, 500 uF. Incubate for 5 min at room temperature.
12. Plate the entire contents of the cuvette on a 10-cm tissue culture plate with feeder cells. The medium on the feeder plate should be changed to M15 prior to plating the cells.
13. Apply G418 selection 24 hr after the electroporation. FIAU selection can also be applied if a positive-negative selection protocol using the herpes simplex virus-1 thymidine kinase (HSV-1 tk) gene is being followed.
14. Refeed the cells when the medium starts turning yellow, usually daily for the first 5 days.
15. Ten days after the electroporation, the colonies are ready to be picked.

E. Picking and Expansion of Colonies after Electroporation

After electroporation, the ES cell colonies take 8-12 days of growth to become visible to the naked eye and can be picked at this time. Care should be taken that only a single colony is seeded per well to avoid a further cloning step. See Ramirez-Solis et al., Methods in Enzymology, 1993.

1. Wash the plate containing the colonies twice with PBS and add PBS to cover the plate.
2. Prepare a 96-well U-bottomed plate by adding 25 ul of trypsin solution per well.
3. Place the original 10-cm plate on an inverted microscope and pick individual colonies with a micropipettor and disposable sterile tips in a maximum volume of 10 ul. Each colony is transferred to the trypsin solution in a well of the plate prepared in Step 2.
4. After 96 colonies have been picked, place the 96-well plate in the 37°, 5% $CO_2$ incubator for 10 min.
5. During the incubation, take a previously prepared 96-well feeder plate (flat-bottomed wells), aspirate the medium, and add 150 ul of M15 per well. Use a multichannel pipettor (12 channels) for all following steps.
6. Retrieve the trypsinized colonies from the incubator and add 25 ul of M15 per well. Break up the clumps of cells by moving the cell suspension up and down with the multichannel pipettor about 5-10 times.
7. Transfer the entire contents of each well to a well in a 96-well plate prepared in Step 5. Change tips each time.
8. Put the plate in the incubator and grow for 3-5 days, changing the medium as necessary.
9. When the wells are approaching confluence, wash twice with PBS and trypsinize using 50 ul of trypsin solution per well during 10 min. Add 50 ul of M15 and break up cell clumps by vigorous pipetting. Replate 50 ul onto a gelatinized 96-well plate without feeder cells. The remaining cells in the original 96-well plate may be frozen by adding 50 ul of 2× freezing medium and proceeding through the next protocol from Step 4.

The gelatinized plate can be grown to confluence for DNA preparation and analysis by "mini-Southern" blotting (Section G). Once the targeted clones have been identified, the appropriate wells can be retrieved from the freezer and expanded for blastocyst injection and further DNA analysis (Section F).

F. Freezing and Thawing ES Cells in 96-Well Plates

Freezing ES clones in individual vials while screening for targeted clones is laborious and time-consuming work, especially if the number of clones to be screened is very large. A strategy has been devised to freeze ES cells in 96-well tissue culture dishes that consistently allows a recovery of 100% of the thawed clones. See Ramirez-Solis et al., Methods in Enzymology, 1993.

1. Change the medium on the cells 4 hr before freezing.
2. Discard the M15 medium by aspiration and rinse the cells twice with PBS.
3. Add 50 ul of trypsin solution per well with the multichannel pipettor and incubate the plate for 10 min at 37°, 5% $CO_2$.
4. Add 50 ul of 2× freezing medium per well and dissociate the colonies.
5. Add 100 ul of sterile light paraffin oil per well to prevent degassing and evaporation during storage at −70°.
6. Seal the 96-well plate with Parafilm and put it into a Styrofoam box; close the box and store it at −70° for at least 24 hr. For long-term storage, transfer the plate to a minus 135° freezer.
7. To thaw, take the 96-well plate out of the freezer and place it into the 37° incubator for 10-15 min.
8. Identify the selected clones and put the entire contents of the well into a 1-cm plate (24-well) with feeder cells containing 2 ml of M 15 medium. Change the medium the next day to remove the DMSO and the oil.

G. Southern Blot Analysis Using DNA Prepared Directly on Multiwell Plates

Screening by Southern blotting necessitates that the colonies be expanded in vitro to provide enough DNA to carry out such an analysis. In this context, it is very important to increase the efficiency of DNA recovery during the extraction process, which will consequently diminish the time that the cells have to be expanded. A replica of the clones may be frozen while carrying out the analysis. A protocol to freeze cells directly in a 96-well plate has been given (Section F). To further improve the efficiency of the gene targeting protocol, a DNA extraction technique that provides a fast, simple, and reliable way to screen a large number of clones by Southern analysis has been developed. After the cell suspensions have been divided into halves and one-half has been frozen, the other is plated on a gelatin-coated 96-well replica plate (Section E). This last plate provides the initial material for the DNA microextraction procedure. Lysis of the cells is carried out in the plate by adding lysis buffer and incubating overnight at 60° in a humid atmosphere. The nucleic acids are precipitated in the plate and remain attached to it while the solution is discarded by simply inverting the plate; the nucleic acids are then rinsed, dried, and the DNA cut with restriction enzymes in the plate. All 96 samples can be separated by electrophoresis in a single gel. This greatly accelerates the rate at which screening can be done by Southern blotting. This protocol has been tested for several restriction enzymes, and all give complete DNA restriction using this procedure. However, a pilot reaction with the enzyme of choice should be performed before starting a large screen. When handling a large number of plates, label bottoms and lids to avoid confusion. See Ramirez-Solis et al., Methods in Enzymology, 1993.

1. Allow the cells on the gelatin-coated plates to grow until they turn the medium yellow every day (4-5 days).
2. When the cells are ready for the DNA extraction procedure, rinse the wells twice with PBS and add 50 ul of lysis buffer per well.
3. Incubate the plates overnight at 60° in a humid atmosphere. This is easily achieved by incubating the plates inside a closed container (Tupperware) with wet paper towels in a conventional 60° oven.
4. The next day, add 100 ul per well of a mix of NaCl and ethanol (150 ul of 5M NaCl to 10 ml of cold absolute ethanol) using a multichannel pipettor.
5. Allow the 96-well plate to stand on the bench for 30 min at room temperature without mixing. The nucleic acids precipitate as a filamentous network.
6. Invert the plate carefully to discard the solution; the nucleic acids remain attached to the plate. Blot the excess liquid on paper towels.
7. Rinse the nucleic acid 3 times by dripping 150 ul of 70% ethanol per well using the multichannel pipettor. Discard the alcohol by inversion of the plate each time.
8. After the final wash, invert the plate and allow it to dry on the bench. The DNA is ready to be cut with restriction enzymes.
9. Prepare a restriction digestion mix containing the following: 1× restriction buffer, 1 mM spermidine, bovine serum albumin (BSA, 100 ug/ml), RNase (100 ug/ml), and 10 units of each restriction enzyme per sample.
10. Add 30 ul of restriction digest mix per well with a multichannel pipettor; mix the contents of the well using the pipette tip and incubate the reaction at 37° overnight in a humid atmosphere.
11. Add gel electrophoresis loading buffer to the samples and proceed to conventional electrophoresis and DNA transfer to blotting membranes. Use a 6 by 10 inch 1% (w/v) agarose gel with three 33-tooth combs spaced 3.3 inches apart. This gives enough space for 96 samples plus one molecular weight marker lane for every comb. Gel electrophoresis in 1×TAE at 80 V for 4-5 hr gives a good separation in the 1-10 kb range.

H. Freezing and Thawing Embryonic Stem Cells in Vials

Clones that appear to have the desired mutation should be expanded and frozen in vials. See Ramirez-Solis et al., Methods in Enzymology, 1993.

1. Dissociate the cells that have been expanded in the 1-cm plate (Section E) with 0.2 ml of trypsin solution for 10 min at 37°, then stop the action of the trypsin by adding 1 volume of M15 and disaggregate the cell clumps as mentioned before.
2. Take the necessary cells for blastocyst injection and for expansion for further DNA analysis, and freeze the rest as follows.
3. Slowly add 1 volume of 2× freezing medium and mix the cell suspension gently.
4. Distribute the cell suspension into aliquots in sterile freezing vials. Place the vials in a Styrofoam container, close it, and store it at −70° overnight. The next day, transfer the vials to a −135° freezer, or to liquid nitrogen.
5. To thaw, transfer the vial containing the frozen cells to a 37° water bath.
6. When the cell suspension has thawed, transfer it to a sterile 15-ml tube. Add M15 medium slowly, while shaking the tube; fill the tube with M15 medium and collect the cells by centrifugation at 1000 rpm for 5 min at room temperature.
7. Discard the supernatant by aspiration, resuspend the cell pellet in 2 ml of M15 medium, ensure the absence of cell clumps, and plate the cell suspension onto a 1-cm plate with feeder cells. Incubate at 37°.

IV. Getting Mutations into the Germ Line

The protocols described to date have all had the aim of generating a mutation in ES cells in such a way that the cells remain totipotent and can thus contribute both to somatic tissues and, most importantly, to the germ line of a cat. Thus, it is important always to grow ES cells on feeder layers, to keep the time in culture to a minimum (particularly at low density), and to dissociate clumps of cells at each passage. To test the pluripotency of each targeted clone, sufficient blastocysts should be injected to give two litters. The sex of the offspring should be determined.

The ES cell lines are usually derived from male blastocysts, and extensive contribution to the injected embryo will convert a female blastocyst to a male animal. This gives a disproportionate number of males in the litter. In addition, males that are converted female blastocysts are desirable, as they transmit only ES cell-derived genes to their offspring. They often have reduced fertility, but this disadvantage is more than offset by the efficient transmission of the mutation by the fertile animal. Experience indicates that if a clone does not give high ES cell contribution chimeras or a good sex distortion in 10-12 offspring, then repeated injections of that clone are unlikely to result in germ line transmission. Male chimeras from those clones should be test bred. Ideally, for any mutation, two clones should be established in the germ line to confirm that the phenotype is the result of the engineered change. Under ideal conditions, 80-90% of injected clones should be transmitted through the germ line. For general discussion of techniques, see Ramirez-Solis et al., Methods in Enzymology, 1993.

A. Aggregation of 8-Cell Stage Embryos with Embryonic Stem Cells

The following procedure is adapted from a protocol described in Stewart, "Production of Chimeras Between Embryonic Stem Cells and Embryos." *Methods in Enzymology*, 1993.

Presently, there are three methods of producing ES cell chimeras: (1) blastocyst injection, (2) morula injection, and (3) morula aggregation. This protocol will use morula aggregation.

All that is necessary for the aggregation procedure is a good stereo dissection microscope with magnification to 40× and a mouth-controlled micropipette. This procedure has also been modified to produce embryos/cats that are entirely derived from the ES cells. This involves the aggregation of ES cells with two tetraploid 4-cell stage embryos. Tetraploid embryos are routinely produced by electrofusion of diploid blastomeres at the 2-cell. Aggregating the diploid ES cells with tetraploid blastomeres results in the ES cells forming most of the ICM, whereas derivatives of the tetraploid embryos tend to form the extraembryonic membranes such as the trophectoderm and yolk sac endoderm. Thus, at birth, the embryo derived from the ICM will be largely or entirely derived from the ES cells. The extraembryonic membranes derived from the tetraploid embryos, in the form of the placenta and yolk sac, are lost at birth.

B. Preparation of 8-Cell Stage Embryos for Aggregation

1. The surgical recovery of embryos are performed by uterine lavage between day 11 and day 13 after onset of FSH and hCG treatment. 8-cell stage embryos are isolated. The embryos are washed twice in M2 to remove any cellular debris, blood cells, etc., and are cultured in drops of CZB plus glucose medium under paraffin oil. See Stewart, supra.

The following steps are described in Verstegen, Journals of Reproduction and Fertility, 1993:

2. To aggregate ES cells with the embryos, it is necessary to remove the zona pellucida. This is done by incubating the embryos for 20-40 sec in dishes of prewarmed (37°) acidified Tyrode's solution. In batches of 10, the 8-cell stage embryos should be introduced into a 35-mm dish containing acidified Tyrode's solution. The low pH of the Tyrode's solution results in the zona pellucida dissolving in the saline solution. The acidified Tyrode's solution should be between pH 2 and 3, if the embryos are to be completely freed of their zonae. As soon as the zona has disappeared, the embryos are removed from the Tyrode's solution and washed 3 times in M2 medium.

3. In a 60-mm bacteriological grade petri dish, set up three 20-ul drops of medium containing a 50:50 mixture of DMEM plus 10% FCS and CZB plus glucose. In addition, set up 20 1-ul drops of the same medium. Cover with light paraffin oil. The three 20-ul drops will hold the ES clumps (see below) that will be aggregated with the embryos. Into each 1-ul drop of medium, transfer two 8-cell stage embryos. The benefit of the small drops is that they not only provide sufficient nutrients for overnight culture, but also physically confine the embryos. When 20 pairs have been set up, the dish is returned to the incubator.

C Preparation of Embryonic Stem Cells for Aggregation

The following procedure is described in Stewart, supra.

1. The ES cells are prepared as small aggregates of between 5 and 10 cells each rather than single cells (which would be difficult to manipulate).

2. A 35- or 60-mm dish of ES cells, in which the cells are growing (in the log phase) as colonies on feeders, is washed twice in $Ca^{2+}/Mg^{2+}$-free PBS. The cells are then covered in $Ca^{2+}/Mg^{2+}$-free PBS containing 0.5 mM EGTA and left for 5 min. This causes the cells in the colonies to loosen their attachment to each other. The loosened colonies of ES cells are drawn up using a mouth-controlled pipette having an internal opening diameter of about 50-75 um with the edges of the tip smoothed by flame polishing. The colonies are then transferred to 20-ul microdrops of 50:50 DMEM plus 10% FCS and CZB medium. By gently blowing the colonies back and forth between the pipette and microdrops, the colonies will fall apart into clumps of ES cells. The clumps are allowed to settle onto the surface of the dish. Individual clumps of 5-10 cells are selected and then introduced into the 1-ul drops containing the two 8-cell stage embryos.

3. The aggregation procedure consists of using a mouth-controlled pipette to push the clump of ES cells into a crevice between two blastomeres. It is important to ensure that the embryos have not started to compact because aggregation with uncompacted embryos is easier and usually results in the clump of cells adhering to the blastomeres. The second embryo is then maneuvered by the pushing/gentle blowing of medium into a position so that it sandwiches the ES clump that is attached to the first embryo. Both embryos must be in contact with each other. Adherence and subsequent aggregation of the ES cells to the embryos are temperature-dependent, and the whole process is more difficult if the dish and embryos are allowed to cool substantially. When all the embryos have been aggregated, the dish is returned to the incubator. Fifteen to twenty minutes later, each aggregate should be checked to ensure that the embryos are still attached to each other and to a clump of ES cells. If a clump of ES cells is not adhering to the embryo (this can be determined by gently blowing the whole aggregate around the microdrop to ensure that all components are sticking to each other), replace the cells with another group. The aggregated ES cells/embryos are then cultured overnight. The following morning, the majority of aggregates should have formed blastocysts. These are then surgically transferred to the uteri of pseudopregnant recipients.

V. Transfer of Embryos to Pseudopregnant Recipient

A. Preparation of Pseudopregnant Recipients

For manipulated embryos to develop to term, they have to be returned to the uterus for proper implantation and development. Female cats must be mated with males for them to initiate the physiological changes associated with pregnancy. If females are mated to normal males, they would contain viable embryos resulting from that mating. The presence of these embryos would compete with any experimentally manipulated embryos transferred to the uteri of the pregnant female. To avoid this but to still induce pregnancy, female recipients are mated with vasectomized males, which can mate with females but cannot fertilize eggs. See Stewart, supra.

B. Vasectomizing Male Cats

The following procedure is described in Stewart, supra.

1. Anesthetize a 4 to 6 month old male cat (Taylor, *The Ultimate Cat Book*, Dorling and Kindersley Ltd., N.Y., N.Y., 1989) by a single injection of Avertin. To make Avertin add 0.5 g of 2,2,2-tribromoethanol to 0.63 ml of tert-amyl alcohol prepared in a 1-ml Eppendorf tube. Vortex to dissolve the tribromoethanol. Add 0.5 ml of this solution to 19.5 ml of prewarmed 0.9% saline solution, in which the anesthetic will dissolve after shaking, and allow to cool. The dose injected is 0.012 ml/g body weight.

2. The anesthetized male is laid on its back, the belly is swabbed with 70% ethanol solution, and a horizontal incision using scissors is made through the skin. All surgical procedures should be performed under a stereo dissection microscope with an incident light source.

3. Expose the underlying peritoneum and make a horizontal incision. This should expose two fat pads.

4. Using a pair of blunt forceps, grasp one of the fat pads and pull it out of the body cavity. This results in the testis also being pulled out with it. Beneath the fat pad and connected to the testis is a muscular tube, the vas deferens. This can be recognized by the single blood vessel that runs along its side.

5. Using a pair of fine forceps, a loop is made in the vas deferens. With a pair of forceps, the tips having been preheated, the loop of vas deferens is cauterized and severed. This results in a section of the tissue being removed, with the remaining ends being sealed.

6. The testis/fat pad is then gently moved back into the peritoneal cavity, and the process is repeated for the other testis.

7. Once the procedure is completed, the peritoneal incision is ligated together using a surgical needle and thread. The skin cut is then clamped together using wound clips.

8. The male is allowed to recover. The animal should be set up and test-mated with females to ensure sterility. The wound clips should be removed 10-14 days after the operation.

C. Transfer of Manipulated Embryos to Pseudopregnant Recipients

For the injected/aggregated embryos to develop to term, they have to be transferred to the uteri of pseudopregnant recipients (i.e., females mated with vasectomized males). For Morula injection/aggregation, transfer occurs the following day, that is, once they have developed to the blastocyst stage, which follows overnight culture in vitro. See Stewart, supra.

It is best to transfer the blastocysts to pseudopregnant recipients whose stage of pregnancy is 1 day behind that of the blastocyst. In normal pregnancy, blastocysts are found in the uteri of day 13 pregnant cats, so the manipulated embryos are transferred to the uteri of day 12 pseudopregnant recipients. This apparently gives blastocysts time to recover in vivo from the in vitro manipulations (Verstegen, *Journals of Reproduction and Fertility,* 1993). Transfer to day 12 recipients also results in a higher incidence of implantation than when blastocysts are transferred to synchronized recipients (i.e., day 12 pregnant females).

If possible, 6-7 embryos should be transferred to each uterine horn. If fewer are available, then transferring to only 1 horn is satisfactory.

1. Female cats that were mated 12 days previously with vasectomized males are anesthetized by an injection of Avertin. Females should be between 18 and 36 months in age (Taylor, *The Ultimate Cat Book*, Dorling and Kindersley Ltd., N.Y., N.Y., 1989).

2. After weighing, the female is injected intraperitoneally with the appropriate volume of Avertine (see section on vasectomizing male cats). The animal should be fully anesthetized within 2-3 min, which is deter-mined by gently squeezing one of the rear paws. If the animal responds by rapidly shaking back and forth, the animal is not anesthetized and needs to be left longer for the anesthetic to take its full effect or be given an additional injection of about one-third the original dose.

3. Once fully anesthetized, the female is laid on its back, the belly is swabbed with 70% ethanol solution, and a horizontal incision using scissors is made through the skin. All surgical procedures should be performed under a stereo dissection microscope with an incident light source. The incision is opened, and some of the transparent mesentery attaching the skin to the peritoneum lying immediately beneath the skin is cut or pulled away. The skin incision is moved over the peritoneum to the point where the right ovary is seen to be lying just beneath the peritoneum. The ovary is recognized by its bright cherry red color (owing to the numerous copora lutea). An incision of no more than 0.5 cm is made through the peritoneum, with care being taken to avoid cutting any of the blood vessels visible in the peritoneum. The ovary is attached to a fat pad and to the oviduct and uterus. By grasping the fat pad, the ovary, oviduct, and uterus are pulled out of the peritoneal cavity with a pair of blunt forceps, exposing the ovarian end of the uterus. To keep the uterus from sliding back into the peritoneal cavity, the fat pad is clamped with a small pair of aneurism clips, which is of sufficient weight to prevent the organ from sliding back. It is important that the uterus not be touched during the surgical procedure, since trauma may result in failure of the embryos to implant.

4. With the ovarian end of the uterus lying on the peritoneum wall, a hole is made in the uterus just above the uterine-oviduct junction, using a new (sterile) 25-gauge syringe needle. It is only necessary to penetrate the wall of the uterus using the tip of this extremely sharp needle, which should be inserted no more than 1-2 mm.

5. The blastocysts to be transferred have, at this point, already been picked up and are lying in the transfer pipette. These pipettes can be readily pulled on a gas or alcohol burner flame. The internal diameter should be about 100 um, and the tip should be no longer than 2-4 cm. Light paraffin oil is drawn into the barrel of the pipette using mouth. The viscosity of the paraffin oil gives a much finer level of control in pipetting medium, which is required for picking up and transferring the blastocysts into the uterine lumen. The embryos to be used for transfer are sitting in a 35-mm dish of prewarmed M2 medium with no paraffin oil covering the medium. The transfer pipette, with the tip filled with paraffin oil, is introduced into the M2 medium. A small amount of medium is drawn up into the tip, followed by a small air bubble. More medium is taken up at about 0.5-1 cm, and then a second small air bubble. This is followed by drawing up 6-7 blastocysts in as small a volume of M2 medium as possible, followed by a third air bubble. The air bubbles act as markers for determining where the embryos are lying, since they are more visible in the pipette than the embryos. The two lowermost bubbles, which sandwich the embryos, indicate where the embryos are lying in the pipette. The first, uppermost bubble acts as a marker to indicate when all the embryos have been transferred into the uterus.

6. Using a pair of fine forceps, grasp the oviduct to steady the uterus. The tip of the transfer pipette is inserted into the hole in the uterine wall and is pushed about 3-5 mm into the uterine lumen. This should be done gently; any resistance indicates that the tip is in contact with the uterine endometrium. Once the transfer pipette has been inserted sufficiently deep into the uterus, it is withdrawn about 1-2 mm to ensure that the opening at the tip (still within the lumen) is not in contact with the endometrium, which would block the exit of embryos into the uterine lumen. The embryos are expelled into the lumen, with the transfer being followed by watching the air bubbles. When the last air bubble (i.e., the one nearest the paraffin oil) is seen to enter the uterus, the pipette is withdrawn. The tip is immediately placed into the dish containing the remaining blastocysts, and medium is gently drawn back and forth through the tip. This cleans any blood that may be adhering to the tip which, if clotted, will block the tip. This washing also ensures that all the embryos were transferred to the uterus. The next set of blastocysts can then be picked up in the transfer pipette using the same arrangement of medium and air bubbles.

7. The uterus into which the embryos were transferred is gently pushed back into the peritoneal cavity after the aneurism clip is removed from the fat pad. The wall is pinched together and can be sutured, although this is not usually necessary. The process is repeated for the remaining uterine horn. When the operation is completed, the edges of the skin where the incisions were made are stapled together by two or three 0.9-mm wound clips (Clay Adams, Becton-Dickinson and Co., Parsippany, N.J.). The recipients are placed on a 370 warmer to keep the cats warm until they regain consciousness. The manipulated embryos should be born within 60-70 days of the day of transfer (Taylor, *The Ultimate Cat Book*, Dorling and Kindersley Ltd., N.Y., N.Y., 1989).

It is possible to knock our both alleles at the ES cell level and generate the homozygous animal directly. Normally, however, the heterozygote cell is injected, and the cats carrying the desired targeted locus are then bred to produce a homozygote See generally, Robbins, Circulation Research 73: 3-9 (1993).

Having described the preferred embodiments of the present invention, it will appear to those ordinarily skilled in the art that various modifications may be made to the disclosed embodiments, and that such modifications are intended to be within the scope of the present invention.

VI. Generation of Allergen-Free Transgenic Animals Using Other Techniques Including Nuclear Transfer While the above procedure describes the use of embryonic stem cells in the production of allergen-free animals, there are other cloning techniques that can be used to create transgenic animals. One such technique is nuclear transfer. In this procedure, the DNA from mature somatic cells can be altered, for example, by transfecting the mature somatic cells with a targeting vector comprising an inactivated allergen gene. When the gene inactivation is confirmed, the donor cells are rendered quiescent in the $G_0$-$G_1$ phase by serum starvation for 3-4 days. These techniques are well-known in the art, see, for example, Wilmut et al. (1997), *Nature* 385:810 and Kato et al., (1998), *Science* 282:2095-2098, which are specifically incorporated herein by reference. These donor cells are fused with enucleated oocytes from the same animal species. Molecules within the embryonic environment cause the differentiated mature DNA to revert back to embryonic DNA. These cells then begin to divide as though they were a part of a newly developing embryo. Thus the derived nuclear transplants are cultured in vitro into blastocysts which are transferred, surgically as described above, or non-surgically, into surrogate mothers at an appropriate time after the onset of estrous. The resulted pregnancy are allowed to carry to term and transgenic animals are delivered, preferably vaginally or with surgical assistance, using established techniques well-know in the art.

Nuclear transfer has been used in mammals as a tool for studying embryogenesis and as a method for the multiplication of embryos. Various live mammalian offspring following nuclear transfer have been obtained from an established cell line. Lambs, for instance, were born after cells derived from sheep embryos, which had been cultured for 6 to 13 passages, were induced to quiesce by serum starvation before transfer of their nuclei into enucleated oocytes. Induction of quiescence in the donor cells may modify the donor chromatin structure to help nuclear reprogramming and allow development. See Campbell et al., Nature 380, 64-66 (1996). It was predicted that nuclear transfer would provide the powerful opportunities for analysis and modification of gene function in other livestock species.

Indeed, before and after that work, scientists have been able to use nuclear transfer to create non-mouse animal clones. Thus, Sims et al., (1993), *Proc. Natl. Acad. Sci. USA* 90:6143-6147 produced calves by transfer of nuclei from cultured inner cell mass cells; Wilmut et al. (1997), *Nature* 385:810 and Schnieke et al. (1997) *Science* 278:2130 demonstrated that nuclei from fetal fibroblast cells have directed the formation of lambs; Cibelli et al. (1998) *Science* 280:1256 cloned cattle cow calves using nuclei from fetal fibroblast cells; Wakayama et al. (1998) *Nature* 394:369 used nuclear transfer to produce fertile mice from cumulus cells collected from metaphase II oocytes; Kato et al., (1998), *Science* 282: 2095-2098 using nuclear transfer technology cloned eight calves from cumulus cells and oviductal cells of a single adult; and Chesne et al., (2002), *Nature Biotechnology*, vol. 20:366-369, used nuclear transfer to produce cloned rabbits. Furthermore, Kuroiwa et al., Nature Genetics, vol. 36, no. 7, pp. 775-780 (2004) and Yang et al., Nature Genetics, vol. 36, no. 7, pp. 671-672, reported on the success of gene targeting in cattle via homologous recombination to specifically modify an immunoglobulin gene. Accordingly, both nuclear transfer and homologous recombination are known to produce cloned animals with modified genotypes.

Nuclear transfer also has been successful in cloning feline cats. Thus, Gomez et al., *Biology Of Reproduction* 69, 1032-1041 (2003), which is incorporated herein by reference, used nuclear transfer to clone African wildcats. In that report, African wild cat and domestic cat fibroblasts were synchronized by one of the following treatments: (1) contact inhibition, (2) serum starvation, or (3) roscovitine; and then nuclear transfer was performed using a micromanipulator (Model MMO-202D; Narishige Instrument, Tokyo, Japan) attached to an inverted microscope (Olympus IX-70, Olympus, Tokyo, Japan) equipped with Hoffman modulation contrast optics and a temperature-controlled stage set at 37° C. (Olympus, Tokai Hit, Japan). Denuded M-II oocytes were incubated for 15 min a salt solution supplemented with nonessential amino acids and other nutrients and then oocytes were enucleated. The first polar body and approximately 10% of the underlying cytoplasm were drawn into an enucleation pipette with subsequent confirmation of removal of the metaphase spindle by epifluorescence microscopy.

Then, Gomez introduced an African wildcat fibroblast cell into the perivitelline space of the enucleated in vivo- or in vitro-matured oocyte. Fusion took place in fusion medium by placing each nuclear transfer couplet between two stainless-steel electrodes attached to micromanipulators and then delivering various pulses perpendicularly to the shared membrane space of the donor cell/cytoplasm.

Following those fusion pulses, the nuclear transfer couplets were washed and cultured and then fusion evaluated visually by confirming the presence or absence of the donor cell in the perivitelline space. To determine if the cell fusion method induces concurrent oocyte activation, in vitro-matured DSH oocytes were electrically pulsed in fusion medium with the presence or absence of calcium by the same procedure as described above, and cultured to determine cleavage frequency.

Activation of the fused couplets was achieved by further pulsing and then the reconstructed couplets and parthenogenetically activated oocytes were cultured until the day of embryo transfer or until Day 8. See Gomez (supra), Materials and Methods section.

Furthermore, Gomez later reported the successful creation of cloned African wildcat kittens. See Gomez et al., Cloning Stem Cells. 2004; 6(3):247-58 ("Birth of African Wildcat cloned kittens born from domestic cats"). Gomez used nuclear transfer and cloned embryos produced by the fusion of African Wildcat fibroblast cell nuclei with domestic cat cytoplasts. Cloned embryos were produced by fusion of a single African Wildcat somatic cell to in vivo or in vitro enucleated domestic cat cytoplasts. Of a total of 17 cloned kittens born, seven were stillborn, eight died within hours of delivery or up to 6 weeks of age, and two were reported alive and healthy. Perinatal mortality was due to lung immaturity at premature delivery, placental separation and bacterial septicemia. Subsequent DNA analysis of 12 cat-specific microsatellite loci confirmed that all 17 kittens were clones of the African Wildcat donor male. Thus, Gomez (2004) reported that the surviving African Wildcat kittens were successfully produced by nuclear transfer. Thus, Gomez recently reported that the successful application of nuclear transfer in cats was demonstrated by the birth of domestic and non-domestic cloned kittens at a similar level of efficiency to that reported for other mammalian species. In cats, it has been demonstrated that either in vivo or in vitro matured oocytes can be used as donor cytoplasts. See Gomez et al., Theriogenology, Volume 66, Issue 1, 1 Jul. 2006, pages 72-81.

Furthermore, Choi et al., Cloning and Stem Cells, Vol. 9, No. 2, pp. 281-290 (2007), incorporated herein by reference, recently reported the successful reproductive fertility of cloned male cats that had been derived from adult somatic cell nuclear transfer. They had used nuclear transfer to successfully produce four cloned cats. See Yin et al., Reproduction, 129, pp. 245-249. There, Yin manipulated various cat oocytes as described above by subjecting the cat cells to the steps of nuclear transfer, in vitro culture of nuclear transfer embryos and cell count, synchronization of recipient females and embryo transfer, microsatellite analysis, and statistical analysis. Briefly, cumulus cells from oocytes were removed by gently pipetting and the resultant denuded oocytes were then cultured. Micromanipulation was then used to place a single nuclear donor cell into the perivitelline space of enucleated ova and then fused via electrofusion. The cloned embryos were then cultured i until embryo transfer.

Then, the fused couplets were then cultured and then the cleavage and blastocyst development of nuclear transfer embryos was evaluated the next day when the number of cells in the blastocysts was evaluated by fluorescence microscopy. Those cloned embryos were then surgically transferred into the oviducts of recipient queens. The cloned embryos at the one-cell stage after fusion or at the two- to four-cell stage after a day of culture were transferred into the oviducts of synchronized females and pregnancy was later determined by palpation 40 or 45 days after embryo transfer and confirmed by X-ray photography at 60 days.

Yin the verified the parentage analysis on the cats successfully obtained by nuclear transfer and the surrogate recipient females to confirm identify of the donor cells used for nuclear transfer. DNA was extracted from ear punches or tail clippings obtained from each newborn cat, recipients and donor cells. Five feline DNA microsatellite markers (FCA229, FCA290, FCA441, FCA201, and FCA224) were used to confirm the genetic identity of the cloned cats, the fetus and the skin cells as donor cells. Hence, Yin concluded that they had produced cloned cats from fetal fibroblast cells of a male donor and from adult somatic cells of a female donor by natural delivery.

Thus, the combination of homologous recombination and nuclear transfer is known to target and introduce specific mutations into somatic cells which can then subjected to nuclear transfer cloning. Hence, Wang & Zhou, Reproductive Biology and Endocrinology, 1:103, 2003, reviewed this successful combination approach of homologous recombination and nuclear transfer for different animal species.

Thus, in accordance to one embodiment of the invention, a transgenic non-human vertebrate animal is produced, wherein the genome of the animal comprises an allergen gene that is inactivated. More preferably, the transgenic animal according to the invention does not produce functional product of the allergen gene. According to another embodiment of the invention, the allergen gene of both the somatic cells and the germ line cells the transgenic animal so produced are inactivated. According to another embodiment of the invention, the transgenic animal is fertile and capable of transmitting the inactivated allergen gene to its offspring.

Accordingly, the present invention established somatic cat cell lines which provide a viable alternative to cat embryonic stem cells for the purpose of targeting the Fel d I gene, as explained in detail in the Examples section below. In short, the invention derived cat somatic cell lines by isolating fetal tissue from the uterine horns of pregnant queens by standard ovariohysterectomy between 3 and 6 weeks of gestation. Connective tissue was then isolated, minced, and incubated whereafter embryonic fibroblasts were separated from remaining undigested tissues. Primary cat somatic cells were then successfully cultured, expanded and frozen following the conditions described for growing embryonic stem cells as described elsewhere in this application. Basically, feline embryonic fibroblasts were grown and then successfully cultured and successfully frozen and thawed. Those cells where then electroporated with exogenous DNA targeting constructs for Fel d I. Cat cells that retained a selectable positive marker gene (the neomycin resistance gene) survived, whereas, cells without the Neo gene died. Similarly, a negative selection marker for survival on ganciclovir by virtue of the absence of the HSV-1 tk gene, helped to further corroborate and identify successful homologous recombination events. Thus, colonies of cat somatic cell lines that survived positive/negative selection were subsequently identified.

The invention also teaches a method for producing a transgenic non-human vertebrate animal comprising an inactivated allergen gene, the method comprising: (a) introducing an animal stem cell comprising an inactivated allergen gene into an animal embryo; (b) transplanting the animal embryo into a pseudopregnant animal; and (c) allowing the animal embryo to mature into an animal.

According to the invention, another preferred method for producing a transgenic non-human vertebrate that comprises an inactivated allergen gene, that does not produce the allergen, and that is homozygous for the inactivated allergen gene, comprises (a) introducing an inactivated animal allergen gene into a cell of the animal; (b) selecting for an animal cell that comprises only the inactivated allergen gene, but not a functional allergen gene; (c) isolating the nucleus of the cell of step (b) comprising the inactivated allergen gene; (d) transferring the nucleus of step (c) into an enucleate egg cell of the animal; (e) transplanting the egg into a pseudopregnant animal and render the animal pregnant; and (f) carrying the pregnancy to term and obtain a transgenic animal. It also is possible according to the present invention to select for cells that have both an inactivated allergen gene and a functional allergen gene, i.e., the cell is heterozygous, and then breed the cloned animals to homozygosity, as described in the preceding passages.

The following examples are given to illustrate the present invention. It should be understood, however, that the invention is not to be limited to the specific conditions or details described in these examples. All published documents referenced herein, including but not limited to US patents, are specifically incorporated by reference.

Example 1

Construction of Targeting Vector

A. Homology Arms

The DNA sequence of a continuous stretch of 22182 base pairs including and surrounding chains 1 and 2 of Fel d I was isolated and identified. The promoter sequence for each chain, and found that both chains share this promoter. Chains 1 and 2 are encoded on complimentary DNA strands, and transcribed in opposite directions (FIG. 7). Additionally, sequences downstream of the 3' end of the genes of chains 1 and 2 were identified.

The assembly of the sequence data containing Fel d I (i) chain 1, (ii) chain 2, (iii) promoter and (iv) the downstream homology arms was performed using Polymerase Chain Reaction (PCR) amplification and DNA sequencing. The published polynucleotide sequence for the Fel d I gene (Griffith et al., Gene, 113(2):263-8, 1992, and Morgenstern et al., Proc. Nat'l. Acad. Sci. USA, 88:9690, 1991), was used as a starting point for a variation of thermal asymmetric interlaced PCR (TAIL-PCR) described in Liu & Whittier, Genomics 25(3): 674-81, 1995.

B. Generation of Homologous Arms

1. Three unidirectional nested forward primers with a high annealing temperature were designed on the published sequence for Fel d I chain 1 and chain 2. See FIGS. 2 and 3.

2. Random primers with a lower annealing temperature were used to amplify the unknown sequence in the reverse direction. The thermal asymmetry of the forward and reverse primers allows for a controlled amplification from the known sequence in chain 1 and chain 2 of Fel d 1. The direction of amplification was controlled by using a high annealing temperature for the forward reaction, followed by a lower temperature for the reverse reaction.

3. Once amplified, the resultant amplified PCR product was used as a template for the second round of amplification using the second nested primer as a source of additional specificity, followed by a third round using the third nested primer.

4. PCR products were analyzed using gel electrophoresis, excised from the agarose gel, cloned into a DNA plasmid, and sequenced using automated dideoxynucleotide dye-terminator sequencing.

5. Oligonucleotide sequencing primers matching the newly generated sequence were then synthesized to complete DNA sequencing of the PCR product, and a continuous sequence was assembled.

6. Once the DNA sequence was complete, the end points of the assembly were used as a starting point for additional cycles of TAIL-PCR reactions. Additional overlapping sequences were assembled into one continuous sequence of x base pairs long. The sequence identity of the upstream promoter sequence of chain 1 and chain 2 allowed for the correct positioning of both chains' sequence data.

7. Nested PCR primers matching the downstream sequence of chain 1 and chain 2 were designed, and long range PCR amplification was used to isolate the homologous arms flanking chain 1 and chain 2. Initial PCR reactions were performed on 200 ng of feline genomic DNA, using Taq polymerase in a reaction buffer containing 10 mM Tris-HCl 50 mM KCl, 1.5 mM MgCl2 at pH 8.3 in a reaction volume of 25 µL. dNTPs were added at a final concentration of 0.4 mM each. 1.5 µL of the first reaction was used as a template for the second reaction using nested or semi-nested primers. Forward and reverse primers were added at a final concentration of 0.4 µM.

8. Cycling conditions for all reactions were: initial denaturation step of 95° C. for 3 minutes, followed by 20 cycles of a denaturation step at 98° C. for 10 s, an annealing step at 60° C. for 20 s, and an extension step at 72° C. for 6 minutes. A final extension step of 10 minutes at 72° C. concluded each reaction.

Primer sequences:
Chain 1 homologous arm:
First reaction:

```
Fwd: ATGACAGAAGAGGATAAGGAGAATGC
Rev: GTAGGCCATTAGATTTTGTATTTGG
```

Second reaction:

```
Fwd: GGATCTTCAAACTGTTTGCACTAGG
Rev: GTTCTTTTTTTCCTTTTAAAAAATGTG
```

Chain 2 homologous arm:
First reaction:

```
Fwd: AGTGTTTCTGATACTAAACAAAGTCCAG
Rev: GTTCTTTACACCTAAAGCTGGAATCC
```

Second reaction:

```
Fwd: GCATTTCTCTGGAATTAAGTGGC
Rev: GTTCTTTACACCTAAAGCTGGAATCC
```

C. Selection Markers

To help detect which cells are correctly targeted, selection markers are added to the vector. Neomycin resistance (neo.sup.r) and Thymidine Kinase (HSV-1 tk) were incorporated into the vector as positive and negative selection markers respectively. The specific concentration of the selection agents, Gentamicin (G418) and gangciclovir, have been determined for cat somatic cell lines.

1. A positive selection cassette was constructed by cloning a Neomycin resistance gene downstream of a murine 3'-phosphoglycerate kinase (PGK) promoter, and upstream of a bovine Growth Hormone poly-adenylation site (bGH-pA). The PGK promoter has been shown to be expressed in almost all eukaryotic cells, including embryonic cells (Adra et al., 1987, Gene 60:65-74). The bGH-pA site is highly effective as a terminator of transcription, and in adding a polyadenine tail to the 3' end of the mRNA. (Campbell, N. A. 1996. Biology, Fourth Edition. Menlo Park, Calif.: Benjamin/Cummings Publishing Company p. 370-374.)

2. The positive selection cassette was cloned in between the Fel dI chain 1 and chain 2 homologous arms. The relative orientation of the homologous arms was conserved, such that the coding sequence of chain 1 and chain 2 and their promoter was replaced in the targeting vector by the positive selection cassette. Upon correct recombination in the cat genome, the entire coding sequence of both genes and the promoter will be replaced by the positive selection cassette.

3. A negative selection cassette was constructed by cloning a HSV-1 tk gene downstream of the MC1 promoter. The MC1 promoter is ubiquitously expressed in almost all cell types (Thomas & Capecchi, 1987, Cell 51:503-512).

4. The negative selection cassette was cloned outside of the targeting vector's homologous arms, so that upon correct recombination in the cat genome, the negative selection cassettes will be excised while the positive selection cassette remains integrated. See FIG. 9.

Example 2

Embryonic Fibroblast Cell Lines

Somatic cat cell lines have been established which provide a viable alternative to cat embryonic stem cells for the purpose of targeting the Fel d I gene.

A. Derivation of Cat Somatic Cell Lines—Feline Embryonic Fibroblasts FEFs

1. Fetal tissue was isolated from the uterine horns of pregnant queens by standard ovariohysterectomy between 3 and 6 weeks of gestation. Extra-embryonic membranes were dissected away from the fetal tissue.

2. Connective tissue was then isolated, minced, and incubated in a basal medium of DMEM containing 2 mg/ml collagenase and 0.25% trypsin at 37 degrees Celsius for 15 minutes with periodic agitation 3. Embryonic fibroblasts were separated from remaining undigested tissues by straining through a 50 micron cell, rinsing with PBS and concentrating by centrifugation.

B. Culture and Expansion of Feline Embryonic Fibroblasts

Primary cat somatic cells were successfully cultured, expanded and frozen following the conditions described for growing embryonic stem cells in section G above.

1. FEFs were grown rapidly in a humidified incubator at 37 degrees Celsius with 5% Carbon dioxide.

2. The FEFs were grown in ES-DMEM medium, but without the addition of Leukemia Inhibitory Factor (LIF). FEF's are passaged without chick serum every 2 or 3 days at a dilution of 1/4 or 1/8 respectively.

3. FEFs were then successfully cultured between 15 and 20 passages, while maintaining stable karyotypes. These FEFs were successfully frozen and thawed.

Example 3

Targeting of Embryonic Somatic Cell Line

Gene targeting in somatic cells has enjoyed years of successes in many different species. We use the vector described above to target Fel d 1 in the feline fibroblast cell line A. Electroporation Cat embryonic somatic cell lines (FEFs) are electroporated with exogenous DNA targeting constructs, as described for cat embryonic stem cells above.

B. Selection

1. Positive Selection of FEFs with Gentamicin (G418): FEF cells that retained the neomycin resistance gene (Neo) survived, when cultured in 500 micrograms of G418 per ml of ES-DMEM, 24 hours after electroporation. Whereas, FEFs without the Neo gene died within 2-7 days of culture in G418.

Negative Selection of FEFs with Ganciclovir: FEFs that retained the HSV-1 tk gene 24 hours after electroporation died within 2-7 days of subsequent culture in ES-DMEM medium containing 500 nanograms of ganciclovir. Whereas, FEF cells that lacked the HSV-1 tk gene survived culture in ganciclovir.

2. Colonies of cat somatic cell lines that survived positive/negative selection were picked 8-10 days after electroporation and expanded, as described above.

C. Confirmation of Successful Recombination by PCR Genotyping

1. DNA is prepared from expanded cell lines that survive positive/negative selection, and PCR amplification is used to verify correct integration in the endogenous Fel d I locus. PCR primers are designed to match DNA sequence right outside the Fel d I chain 1 homologous arm and in the polyadenylation site (bGH-pA) of the positive selection marker; and right outside the chain 2 homologous arms and inside the promoter sequence (PGK) of the positive selection marker. Only correct targeting of Fel d I, in which recombination events in both homologous arms replace the Fel d I chain 1, chain 2 and promoter, brings the forward and reverse primers within a short enough distance to allow PCR amplification.

2. PCR reactions are performed as described above. Cycling conditions for all reactions are as follows: initial denaturation step of 95° C. for 3 minutes, followed by 40 cycles of a denaturation step at 98° C. for 10 s, an annealing step at 60° C. for 20 s, and an extension step at 72° C. for 7 minutes. A final extension step of 10 minutes at 72° C. concluded each reaction.

Primer sequences:

bGH-pA site—Chain 1 homologous arm:

```
Fwd: CGACTGTGCCTTCTAGTTGCC
Rev: GTAGGCCATTAGATTTTGTATTTGG
```

Chain 2 homologous arm—PGK:

```
Fwd: AGTGTTTCTGATACTAAACAAAGTCCAG
Rev: TTGTGTAGCGCCAAGTGCC
```

D. Confirmation of Successful Recombination of the Fel d1 Locus in FEFs Using Fluorescent In Situ Hybridization (FISH)

1. Preparation of Mitotic Spreads of Feline Embryonic Fibroblasts

Actively growing plates of FEFs are cultured in ES-DMEM containing 1.5 micrograms of colcemid per ml for two hours. The medium is removed and replaced by PBS. The plates are tapped gently to detach the dividing cells that loosen more readily. The cells in the supernatant are pelleted by centrifugation and the supernatant removed. Cells are resuspended in 1 ml of a hypotonic solution of 0.075 M KCl and incubated at room temperature for 20 minutes to lyse the cells cytoplasmic membranes. The cell suspension is fixed with one drop of a solution containing 3 parts methanol and one part acetic acid. The pellet is centrifuged at 1000 RPM for 5 minutes, and resuspended in 2 ml of fixative. This procedure is repeated 3-5 times until the there are no clumps in the suspension. Mitotic chromosome spreads are made by dropping drops of the cell suspension onto glass slides and allowing them to air dry.

2. Preparation of Probes for Two Color-FISH

A green fluorescent probe is made from the cloned Fel d1 chain 1 and chain 2 homology arms and labeled by nick translation with Fluoroscein-dUTP and DNA polymerase I in a translation buffer (New England Nuclear). A second red fluorescent probe is generated for the foreign gene portion of the targeting construct containing the PGK-Neo cassette by nick translation with biotinylated-dUTP. This probe is visualized and the signal amplified by incubating with strepavidin conjugated with Texas Red. The green probe serves as a positive control for successful hybridization to the Fel d 1 locus, as it binds to both of the targeted and non-targeted alleles. The red probe binds to the foreign PGK-NEO sequence in the targeted allele. The two probes co-localize to the properly targeted Fel d 1 locus, and their superimposition appears, as a yellow signal under fluorescent microscopy.

3. Hybridization of Probes to Slides

Mitotic spreads are treated with 200 micrograms of pancreatic RNAse-A per ml of 2×SSC solution (0.3M Sodium chloride, 0.03M sodium citrate at pH 7.0) at 37 degrees Celsius for 1 hour. Slides are then washed 4 times in 2×SSC for 5 minutes and then dehydrated in a series of 70%, 80% 90% and 95% solutions of ethanol and water for 5 minutes each at room temperature. Slides are then denatured in a solution of 70% formamide in 2×SSC for 2 minutes, and then dehydrated again in the same ethanol series at 4 degrees Celsius. Ten nanograms of each labeled probe is diluted in a hybridization solution containing 50% formamide, 10% dextran sulfate, 2×SCC, 20 mM sodium phosphate, 10×Denhardt's solution and 5 micrograms of sheared salmon sperm DNA. The probe mixture is denatured at 70 degrees Celsius for 5 minutes and then placed on ice prior. The slides are hybridized with the probe solution by incubating for 16 hours at 37 degrees Celsius. The slides are washed 5 times in 2×SSC containing 50% formamide for 5 minutes followed by 5 washes if 2×SSC for 5 minutes all at 40 degrees Celsius prior to visualization by fluorescent microscopy.

E. Confirmation of Successful Recombination of the Fel d1 Locus in Somatic Cell Lines (FEFs) by Southern Blot Analysis Successful recombination of the Fel d I locus in somatic cell lines can be readily determined using conventional Southern Blot analysis, such as by employing the following steps:

1. Allow the cells on the gelatin-coated plates to grow until they turn the medium yellow every day (4-5 days).
2. When the cells are ready for the DNA extraction procedure, rinse the wells twice with PBS and add 50 ul of lysis buffer per well.
3. Incubate the plates overnight at 60° in a humid atmosphere. This is easily achieved by incubating the plates inside a closed container (Tupperware) with wet paper towels in a conventional 600 oven.
4. The next day, add 100 ul per well of a mix of NaCl and ethanol (150 ul of 5M NaCl to 10 ml of cold absolute ethanol) using a multichannel pipettor.
5. Allow the 96-well plate to stand on the bench for 30 min at room temperature without mixing. The nucleic acids precipitate as a filamentous network.
6. Invert the plate carefully to discard the solution; the nucleic acids remain attached to the plate. Blot the excess liquid on paper towels.
7. Rinse the nucleic acid 3 times by dripping 150 ul of 70% ethanol per well using the multichannel pipettor. Discard the alcohol by inversion of the plate each time.
8. After the final wash, invert the plate and allow it to dry on the bench. The DNA is ready to be cut with restriction enzymes.
9. Prepare a restriction digestion mix containing the following: 1× restriction buffer, 1 mM spermidine, bovine serum albumin (BSA, 100 ug/ml), RNase (100 ug/ml), and 10 units of each restriction enzyme per sample.
10. Add 30 ul of restriction digest mix per well with a multichannel pipettor; mix the contents of the well using the pipette tip and incubate the reaction at 37° overnight in a humid atmosphere.
11. Add gel electrophoresis loading buffer to the samples and proceed to conventional electrophoresis and DNA transfer to blotting membranes. Use a 6 by 10 inch 1% (w/v) agarose gel with three 33-tooth combs spaced 3.3 inches apart. This gives enough space for 96 samples plus one molecular weight marker lane for every comb. Gel electrophoresis in 1×TAE at 80 V for 4-5 hr gives a good separation in the 1-10 kb range.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. An isolated nucleic acid comprising at least 900 contiguous nucleotides of the sequence depicted in SEQ ID NO. 7.

2. An isolated polynucleotide comprising a sequence of at least about 400 bp from nucleotides 1-14,700 of SEQ ID NO. 7, wherein the polynucleotide is homologous to, and capable of recombining with, a locus of the feline cell genome adjacent to an endogenous Fel d 1 gene.

3. An isolated polynucleotide comprising a sequence of at least about 700 bp from nucleotides 10,831-21,939 of SEQ ID NO. 7, wherein the polynucleotide is homologous to, and capable of recombining with, a locus of the feline cell genome adjacent to an endogenous Fel d 1 gene.

4. An isolated Fel d 1 promoter sequence comprising a sequence from nucleotides 10,831-14,719 of SEQ ID NO. 7, which is capable of expressing a polynucleotide to which it is operably linked.

5. A homologous recombination vector, comprising: (1) a first homology arm, (2) a desired polynucleotide, and (3) a second homology arm, wherein the desired polynucleotide is positioned between the first and second homology arms, and wherein each of the first and second homology arms comprises at least about a 700 bp sequence of SEQ ID NO. 7.

6. The homologous recombination vector of claim 5, wherein the first homology arm comprises at least about 100 bp of the region between nucleotide 1 to about nucleotide 8,800 of SEQ ID NO. 7.

7. The homologous recombination vector of claim 5, wherein the first homology arm comprises at least about 100 bp of the region between nucleotide 1 to about nucleotide 10,000 of SEQ ID NO. 7.

8. The homologous recombination vector of claim 5, wherein the first homology arm comprises at least about 100 bp of the region between nucleotide 1 to about nucleotide 10,800 of SEQ ID NO. 7.

9. The homologous recombination vector of claim 5, wherein the first homology arm comprises at least about 100 bp of the region between nucleotide 1 to about nucleotide 14,800 of SEQ ID NO. 7.

10. The homologous recombination vector of claim 5, wherein the second homology arm comprises at least about 100 bp of the region between about nucleotide 16,000 to nucleotide 21,939 of SEQ ID NO. 7.

11. The homologous recombination vector of claim 5, wherein the second homology arm comprises at least about 100 bp of the region between about nucleotide 14,700 to nucleotide 21,939 of SEQ ID NO. 7.

12. The homologous recombination vector of claim 5, wherein the second homology arm comprises at least about 100 bp of the region between about nucleotide 10,800 to nucleotide 21,939 of SEQ ID NO. 7.

13. The homologous recombination vector of claim 5, wherein either or both of the homology arms comprises a SEQ ID NO. 7 sequence that has a length selected from the group consisting of about 1 kb long, about 2 kb long, about 3 kb long, about 4 kb long, about 5 kb long, about 6 kb long, about 7 kb long, about 8 kb long, about 9 kb long, and about 10 kb long.

14. The homologous recombination vector of claim 5, wherein the desired polynucleotide is a selectable marker.

15. A homologous recombination vector, comprising (1) a first homology arm comprising a sequence of at least about 100 bp from nucleotides 1-8,437 of SEQ ID NO. 7; (2) a second homology arm comprising, a sequence of at least about 100 bp from nucleotides 16029-21939 of SEQ ID NO. 7; and (3) a desired polynucleotide that is positioned in between the first and second homology arms, wherein the first and second homology arms are homologous to, and capable of recombining with, a feline cell genome's Fed d 1 locus.

16. The homologous recombination vector of claim 5, wherein the length of the first and second homology arms is selected from the group consisting of at least about 800, at least about 900, or at least about 1000 consecutive nucleotides of SEQ ID NO. 7.

* * * * *

UNITED STATES PATENT AND TRADEMARK OFFICE
CERTIFICATE OF CORRECTION

| | | |
|---|---|---|
| PATENT NO. | : 8,119,785 B2 | Page 1 of 1 |
| APPLICATION NO. | : 11/979151 | |
| DATED | : February 21, 2012 | |
| INVENTOR(S) | : Avner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this
Seventh Day of August, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,119,785 B2 | Page 1 of 1 |
| APPLICATION NO. | : 11/979151 | |
| DATED | : February 21, 2012 | |
| INVENTOR(S) | : Avner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Eleventh Day of September, 2012

David J. Kappos
*Director of the United States Patent and Trademark Office*